US010806819B2

(12) United States Patent
Shuler

(10) Patent No.: US 10,806,819 B2
(45) Date of Patent: Oct. 20, 2020

(54) WOUND COVERINGS COMPRISING VITAMIN D AND RELATED METHODS

(71) Applicant: Marshall University Research Corporation, Hungtington, WV (US)

(72) Inventor: Franklin D. Shuler, Huntington, WV (US)

(73) Assignee: MARSHALL UNIVERSITY RESEARCH CORPORATION, Huntington, WV (US)

( * ) Notice: Subject to any disclaimer, the term of this patent is extended or adjusted under 35 U.S.C. 154(b) by 93 days.

(21) Appl. No.: 15/541,954

(22) PCT Filed: Jan. 15, 2016

(86) PCT No.: PCT/US2016/013574
§ 371 (c)(1),
(2) Date: Jul. 6, 2017

(87) PCT Pub. No.: WO2016/115448
PCT Pub. Date: Jul. 21, 2016

(65) Prior Publication Data
US 2018/0000980 A1   Jan. 4, 2018

Related U.S. Application Data

(60) Provisional application No. 62/103,679, filed on Jan. 15, 2015.

(51) Int. Cl.
*A61L 15/44* (2006.01)
*A61K 31/59* (2006.01)
(Continued)

(52) U.S. Cl.
CPC .............. *A61L 15/44* (2013.01); *A61K 31/59* (2013.01); *A61K 31/74* (2013.01); *A61L 15/225* (2013.01);
(Continued)

(58) Field of Classification Search
CPC ........ A61L 15/44; A61L 15/26; A61L 15/425; A61L 15/64; A61L 15/225;
(Continued)

(56) References Cited

U.S. PATENT DOCUMENTS

2004/0009210 A1* 1/2004 Koenig ................. A61L 15/225
424/445
2006/0083784 A1* 4/2006 Ignatious ................ A61P 9/06
424/464
(Continued)

FOREIGN PATENT DOCUMENTS

WO   2006/094064 A2   9/2006
WO   WO-2006094064 A2 * 9/2006 ........... A61K 9/0014

OTHER PUBLICATIONS

United States Patent and Trademark Office, International Search Report and Written Opinion issued in corresponding Application No. PCT/US2016/013574, dated Mar. 31, 2016.
(Continued)

*Primary Examiner* — Robert A Wax
*Assistant Examiner* — Quanglong N Truong
(74) *Attorney, Agent, or Firm* — Stiles & Harbison, PLLC; Terry L. Wright

(57) ABSTRACT

A wound covering is provided that comprises a substrate and vitamin D, or analogues or metabolites thereof, embedded in the substrate. Methods of making a wound covering are also provided and include the steps of providing a solution that includes a polymer; adding vitamin D, or analogues or metabolites thereof, to the solution to form a mixture; and forming one or more fibers from the mixture that are then embedded with the vitamin D, or analogues or metabolites thereof. Methods of treating a subject are further provided and include the step of applying a wound covering including one or more fibers embedded with vitamin D, or analogues or metabolites thereof, to a site on a subject.

18 Claims, 13 Drawing Sheets

(51) Int. Cl.
  A61K 31/74    (2006.01)
  A61L 15/22    (2006.01)
  A61L 15/26    (2006.01)
  A61L 15/42    (2006.01)
  A61L 15/64    (2006.01)

(52) U.S. Cl.
  CPC ............ *A61L 15/26* (2013.01); *A61L 15/425* (2013.01); *A61L 15/64* (2013.01); *A61L 2300/406* (2013.01); *A61L 2300/41* (2013.01); *A61L 2300/428* (2013.01); *A61L 2300/602* (2013.01); *A61L 2300/62* (2013.01)

(58) Field of Classification Search
  CPC ........... A61L 2300/406; A61L 2300/62; A61L 2300/428; A61L 2300/602; A61L 2300/41; A61K 31/59; A61K 31/74
  See application file for complete search history.

(56) References Cited

U.S. PATENT DOCUMENTS

| | | | | |
|---|---|---|---|---|
| 2009/0112236 | A1* | 4/2009 | Stopek | A61L 17/12 606/151 |
| 2010/0273748 | A1* | 10/2010 | Gallo | A61K 31/593 514/167 |
| 2013/0266664 | A1* | 10/2013 | Yang | D04H 1/587 424/618 |
| 2014/0004159 | A1* | 1/2014 | Xie | A61L 27/00 424/400 |

OTHER PUBLICATIONS

Reichman D.E., et al. Reducing Surgical Site Infections: A Review. Rev Obstet Gynecol. 2009; 2(4): 212-221.

Peleg AY, et al. Acinetobacter baumannii: Emergence of a Successful Pathogen. Clin Microbiol Rev. 2008; 21(3): 538-582.

Kahlenberg JM, et al. Little Peptide, Big Effects: The Role of LL-37 in Inflammation and Autoimmune Disease. J Immunol. 2013; 191(10): 4895-4901.

Steinstraesser L, et al. Skin Electroporation of a Plasmid Encoding hCAP-18/LL-37 Host Defense Peptide Promotes Wound Healing. Mol Ther. 2014; 22(4): 734-742.

Liu PT, et al. Toll-like receptor triggering of a vitamin D-mediated human antimicrobial response. Science. 2006; 311 (5768): 1770-1773.

Dixon BM, et al. Positive correlation between circulating cathelicidin antimicrobial peptide (hCAP18/LL-37) and 25-hydroxyvitamin D levels in healthy adults. BMC Res Notes. 2012; 5(1): 575.

Wang Q, et al. Effects of 25-hydroxyvitamin D3 on cathelicidin production and antibacterial function of human oral keratinocytes. Cell Immunol. 2013; 283(1-2): 45-50.

Gombart A. The vitamin D-antimicrobial peptide pathway and its role in protection against infection. Fut Microbiol 2009; 4(9): 1151-1165.

Hewison, M. Vitamin D and the immune system: new perspectives on an old theme. Endocrin Metab Clin 2010; 39(2): 365-379.

Jiang J, Chen G, Shuler FD, Wang C-H and Xie J. 2015. Local sustained delivery of 25-hydroxyvitamin D3 for prevention of surgical site infections. Pharm Res. 2015; 32(9): 2851-2862.

Maruotti, N, et al. Vitamin D and the Immune System. The Journal of Rheumatology 2010: 491-495.

Shuler, FD, et al. Antibiotic-Like Actions of Vitamin D. W V Med J 109(1): 22-25.

* cited by examiner

WOUND COVERINGS COMPRISING VITAMIN D AND RELATED METHODS

RELATED APPLICATIONS

This application claims priority from U.S. Provisional Application Ser. No. 62/103,679, filed Jan. 15, 2015, the entire disclosure of which is incorporated herein by this reference.

TECHNICAL FIELD

The presently-disclosed subject matter relates to wound coverings comprising vitamin D, or analogues or metabolites thereof, and related methods. In particular, the presently-disclosed subject matter relates to wound coverings and related methods that make use of substrates that are embedded with vitamin D, or analogues or metabolites thereof.

BACKGROUND

Surgical site infections (SSI's) account for up to 38% of all nosocomial infections, creating a significant impact on morbidity and mortality. Over 290,000 SSI's occur per annum with an estimated inpatient hospital cost of over $10 billion. Postsurgical infections lead to increased length of postoperative hospital stay, escalated expenses, higher rates of hospital readmission, and jeopardized health outcomes including a 3% risk of mortality. Antibiotic resistance has become a significant issue to current evidence based treatment protocols. For example, multi-drug resistant nosocomial strains of bacteria such as *Acinetobacter baumannii* and carbapenem-resistant *Enterobacteriaceae* (CRE-"nightmare bacteria"), which kills up to 50% of infected patients, have become a major challenge for treatment of SSIs and wounds, underscoring the need for novel approaches to supplement current antimicrobial based treatment strategies.

Human cathelicidin LL-37 is a small cationic peptide that can reduce SSI's and can act as an antibiotic through membrane disruption. LL-37 is derived from an inactive proform (hCAP-18) produced in humans by various types of cells (e.g., keratinocytes, monocytes, neutrophils, macrophages, and epithelial cells) following exposure to active vitamin D (1.25-dihydroxyvitamin $D_3$-1.25$(OH)_{2D}$) with local production critically dependent on the storage form of vitamin D (25-hydroxyvitamin D3-25(OH)D). Direct peptide application and over expression following gene therapy approaches have been used to alter local concentrations of LL-37, but significant issues have developed precluding this direct approach, including toxicity to eukaryotic cells, formation of toroidal pore, and risk of unintended and undesired tissue destruction and inflammation in the area of surgical incision.

Hence, there remains a need for compositions, including wound coverings, that effectively minimize the risk of SSIs while avoiding direct application of LL-37.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this Summary does not list or suggest all possible combinations of such features.

The presently-disclosed subject matter includes wound coverings comprising vitamin D, or analogues or metabolites thereof, and related methods. In particular, the presently-disclosed subject matter includes wound coverings and related methods that make use of substrates that are embedded with vitamin D, or analogues or metabolites thereof.

In some embodiments of the presently-disclosed subject matter, a wound covering is provided that comprises a substrate and vitamin D, or analogues or metabolites thereof, embedded in the substrate, such as a substrate comprised of either man-made or natural fibers. In some embodiments, the substrate includes one or more fibers that are comprised of a polymer such as, in some embodiments, poly(ε-caprolactone) (PCL), poly($_L$-lactide) (PLA), cellulose, or combinations thereof. In some embodiments, the fiber is an electrospun fiber. In some embodiments, the one or more fibers form a mesh or a wound dressing. In some embodiments, the wound covering is biodegradable and/or biocompatible.

Regardless of the particular form of the wound coverings described herein, in some embodiments, an exemplary wound covering of the presently-disclosed subject matter is configured to release vitamin D, or analogues or metabolites thereof, under physiological conditions for at least about 1 day to about 50 days. In some embodiments, the wound coverings further comprise a bioactive agent, such as, in some embodiments, antibiotics, anti-inflammatories, and combinations thereof.

Further provided by the presently-disclosed subject matter are methods for making a wound covering. In some embodiments, a method for making a wound covering is provided that comprises the steps of: providing a solution that includes a polymer; adding vitamin D, or analogues or metabolites thereof, to the solution to form a mixture; and forming one or more fibers from the mixture that are embedded with the vitamin D, or analogues or metabolites thereof. In some embodiments, the step of forming the one or more fibers comprises electrospinning the mixture to form the one or more fibers. In some embodiments, the one or more fibers are further exposed to a plasma treatment.

Still further provided, in some embodiments of the presently-disclosed subject matter, are methods of treating a subject. In some embodiments, a method of treating a subject is provided that comprises applying a wound covering to a site on a subject, where the wound covering includes one or more fibers that are embedded with vitamin D, or analogues or metabolites thereof. In some embodiments, the site on the subject is a surgical site or a site of a tissue injury or wound. In some embodiments, applying the wound covering increases an amount of an antimicrobial peptide in the subject, including, in certain embodiments, hCAP18 and LL-37.

Further features and advantages of the present invention will become evident to those of ordinary skill in the art after a study of the description, figures, and non-limiting examples in this document.

Figure 1A:
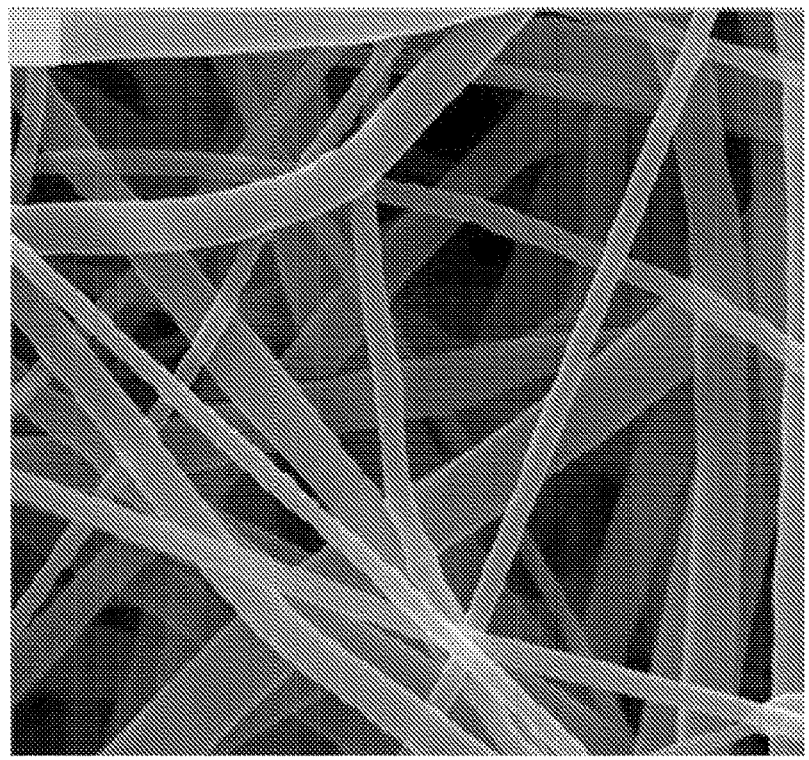
FIGS. 1A-1D include scanning electron microscope (SEM) images showing (FIG. 1A) poly(ε-caprolactone)
Figure 1B:
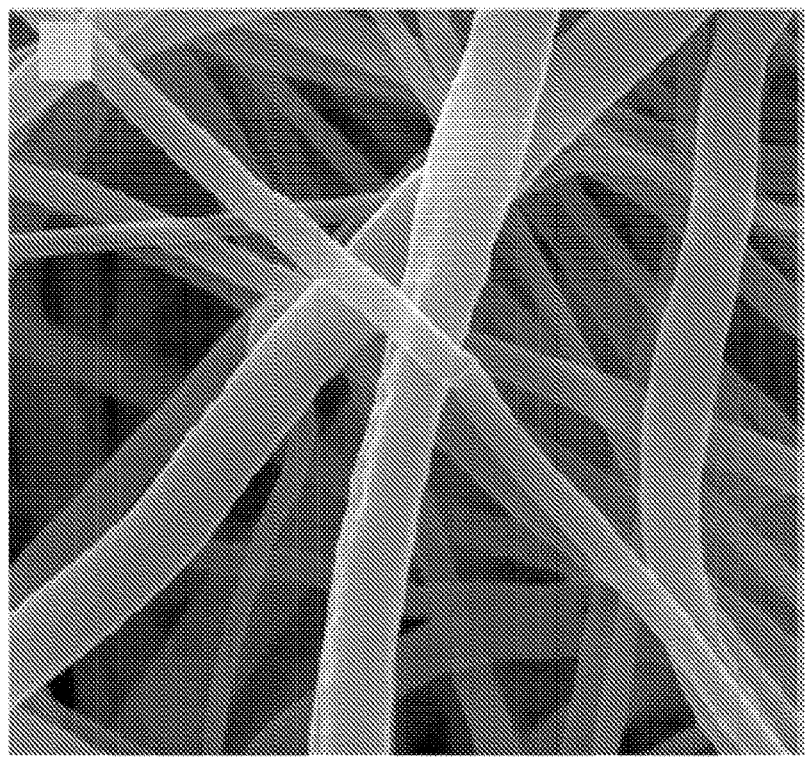
Figure 1C:
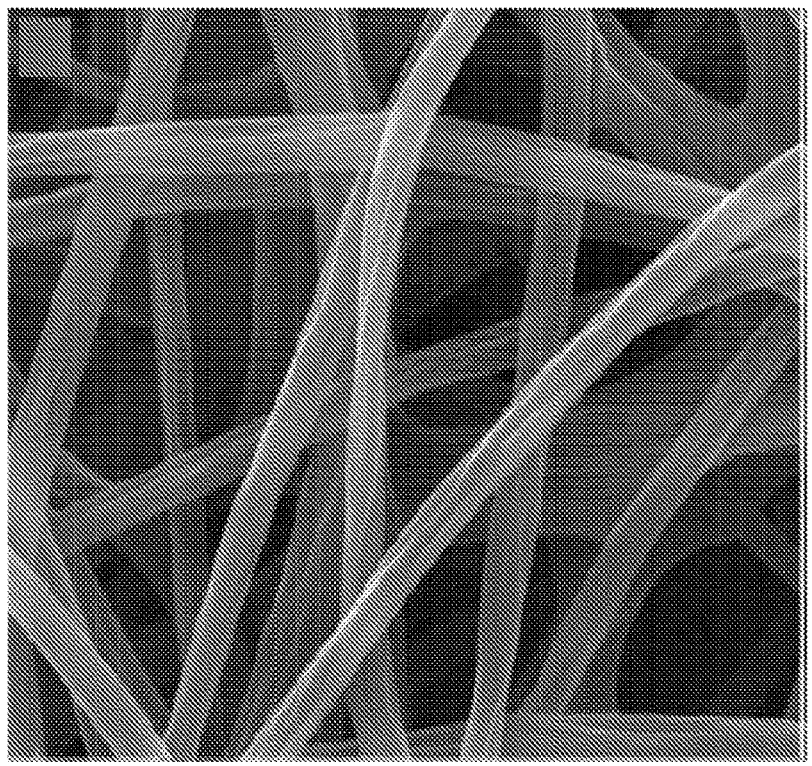
Figure 1D:
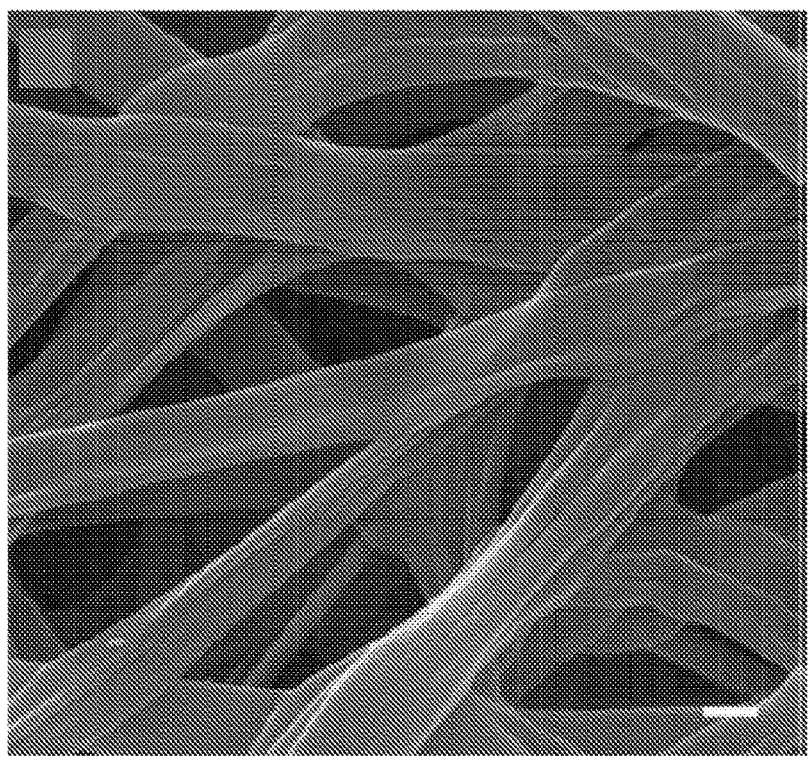
Figure 2A:
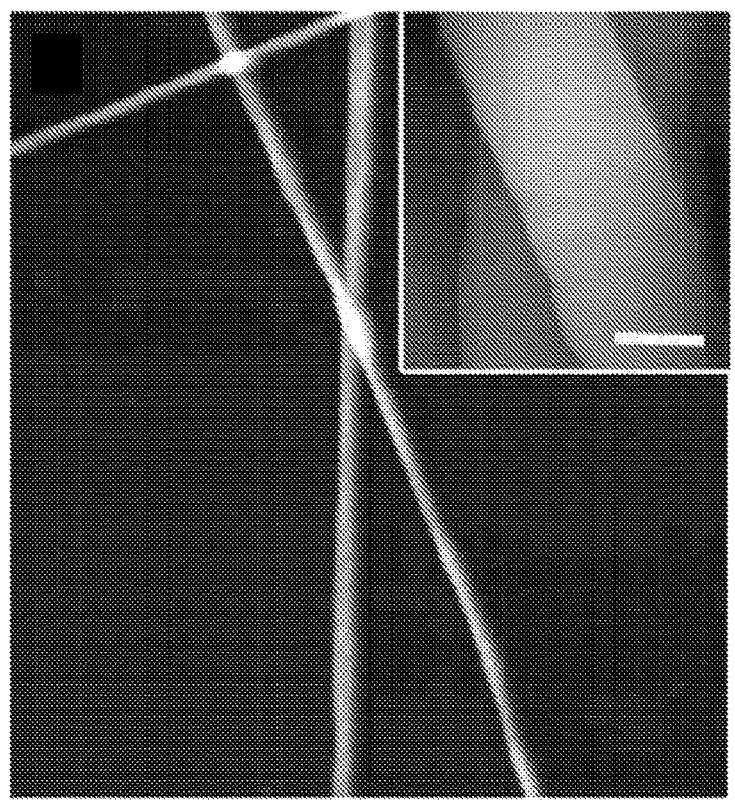
Figure 2B:
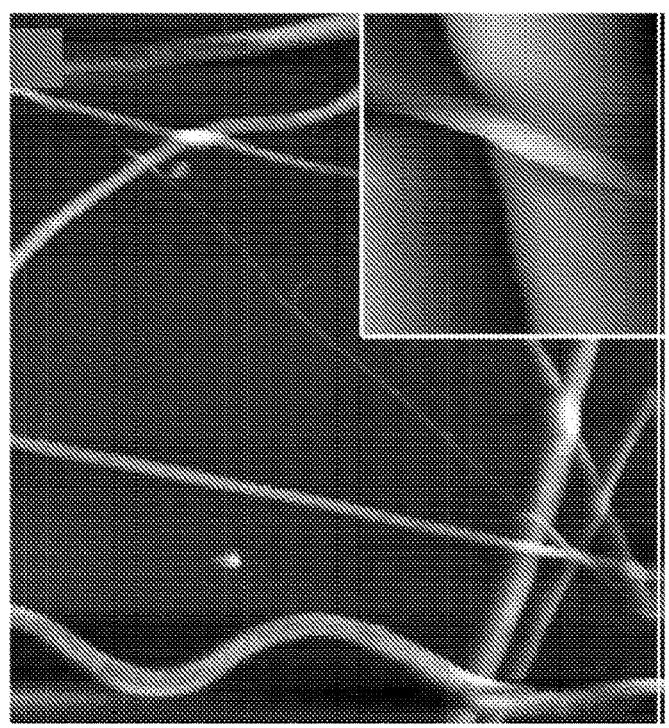
Figure 2C:
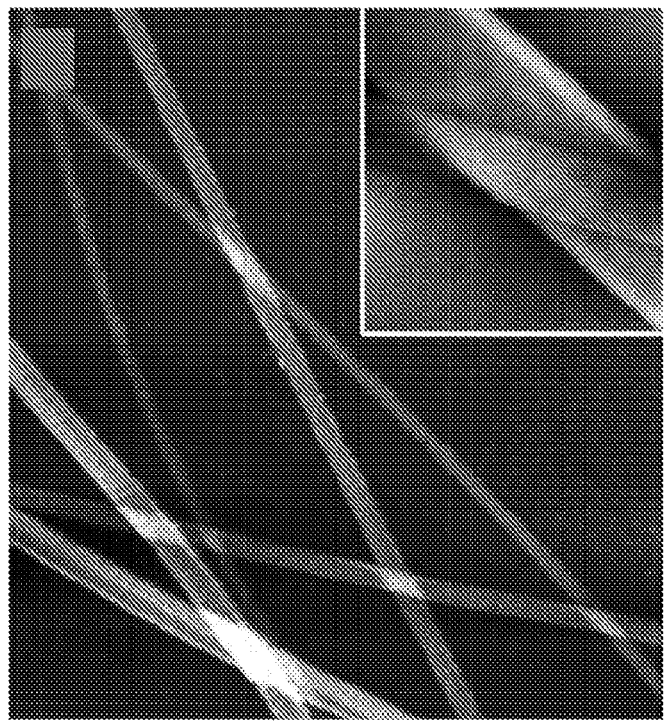
Figure 2D:
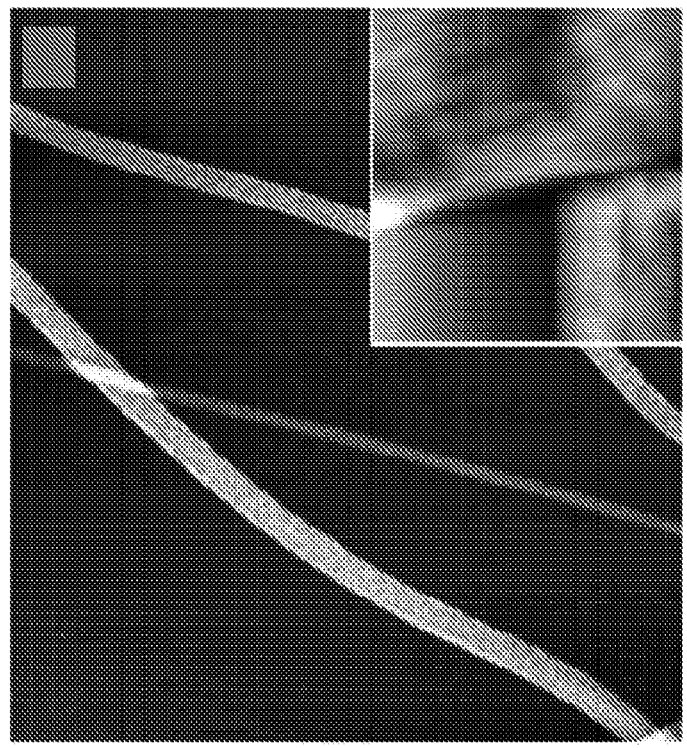
Figure 3A:
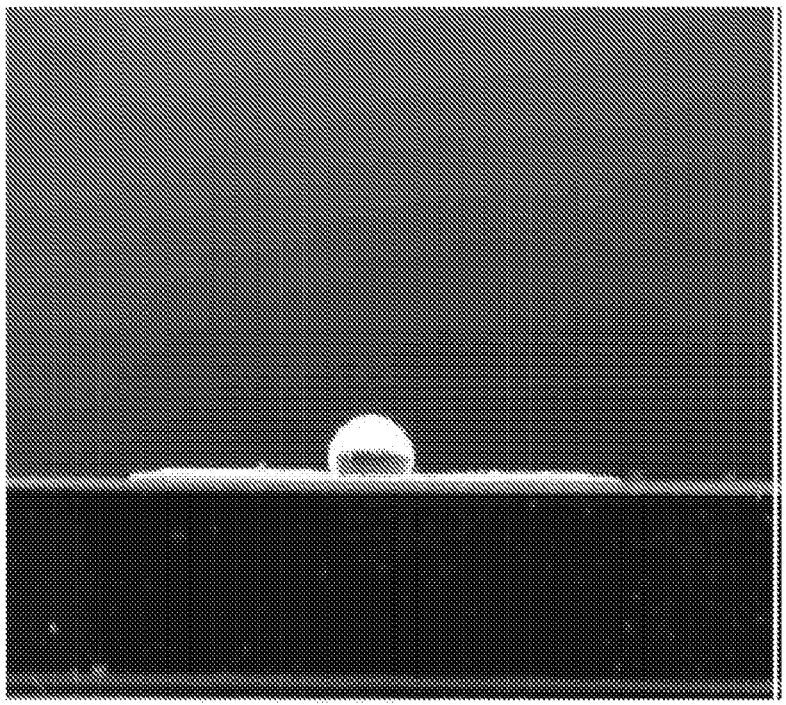
Figure 3B:
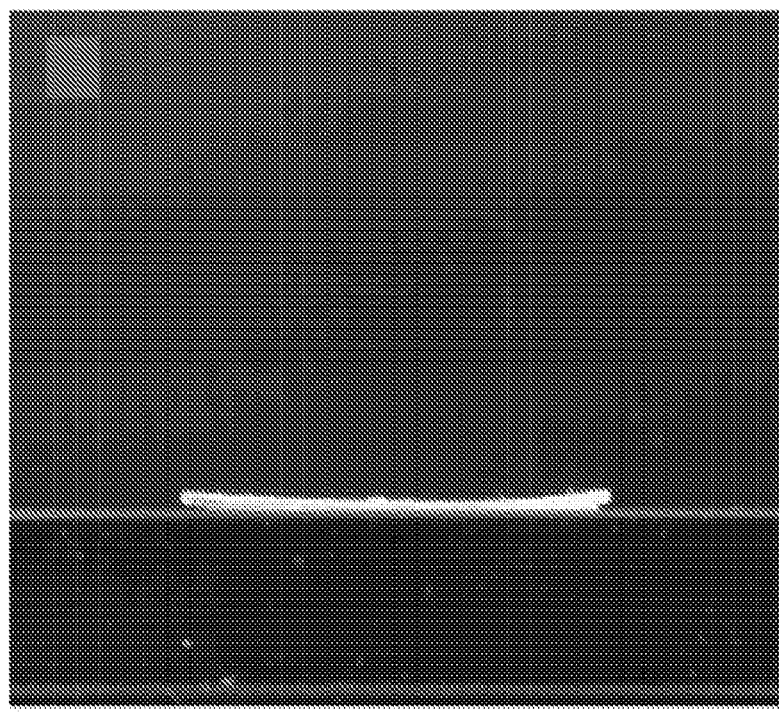
Figure 3C:
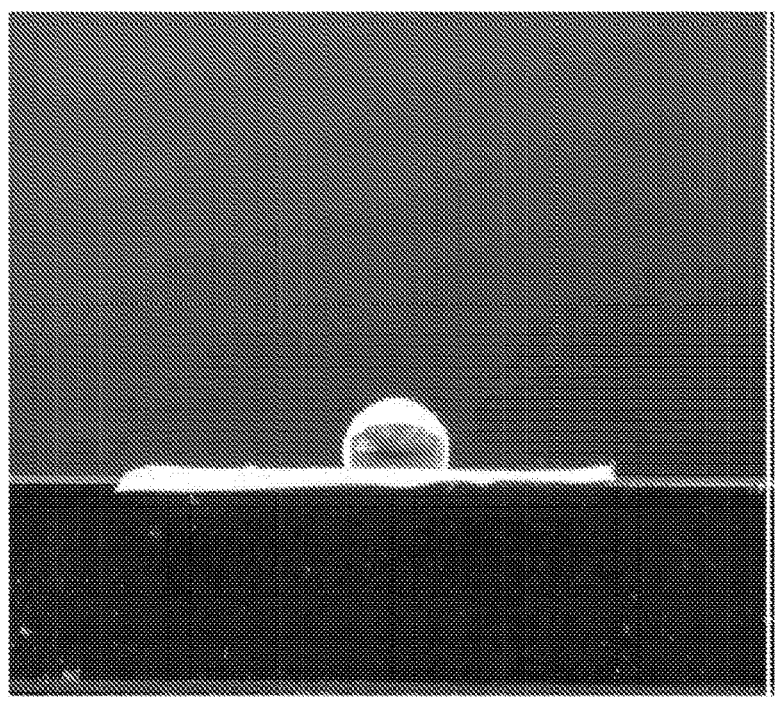
Figure 3D:
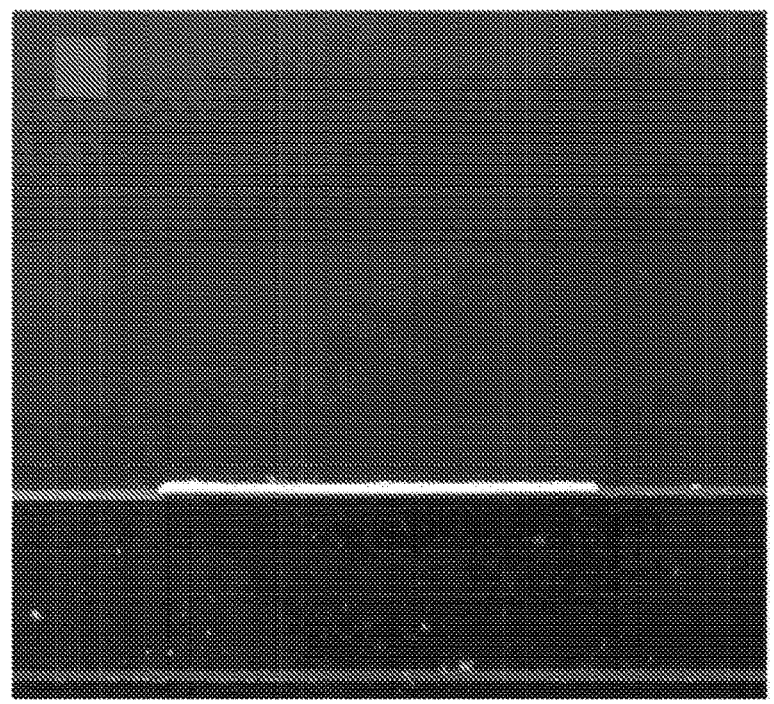

(PCL) fibers, (FIG. 1B) 25-hydroxyvitamin $D_3$ (25 (OH) D) loaded PCL fibers, (FIG. 1C) poly($_L$-lactide) (PLA) fibers, and (FIG. 1D) 25 (OH) D loaded PLA fibers. The scale bar is 1 µm.

FIGS. 2A-2D include atomic force microscope (AFM) images showing (FIG. 2A) PCL fibers, (FIG. 2B) 25(OH)D loaded PCL fibers, (FIG. 2C) PLA fibers, and (FIG. 2D) 25(OH)D loaded PLA fibers. The scale bar in the inset is 1 µm.

FIGS. 3A-3D include images showing water contact angles before and after air plasma treatment on samples comprised of (FIG. 3A) PCL fibers, (FIG. 3B) plasma treated PCL fibers, (FIG. 3C) PLA fibers, and (FIG. 3D) plasma treated PLA fibers.

Figure 4A:
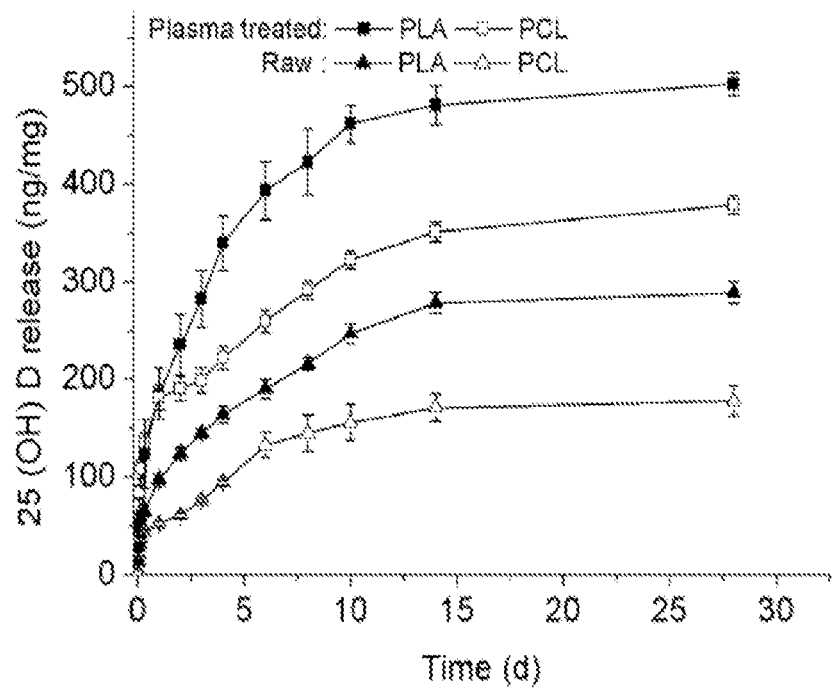
Figure 4B:
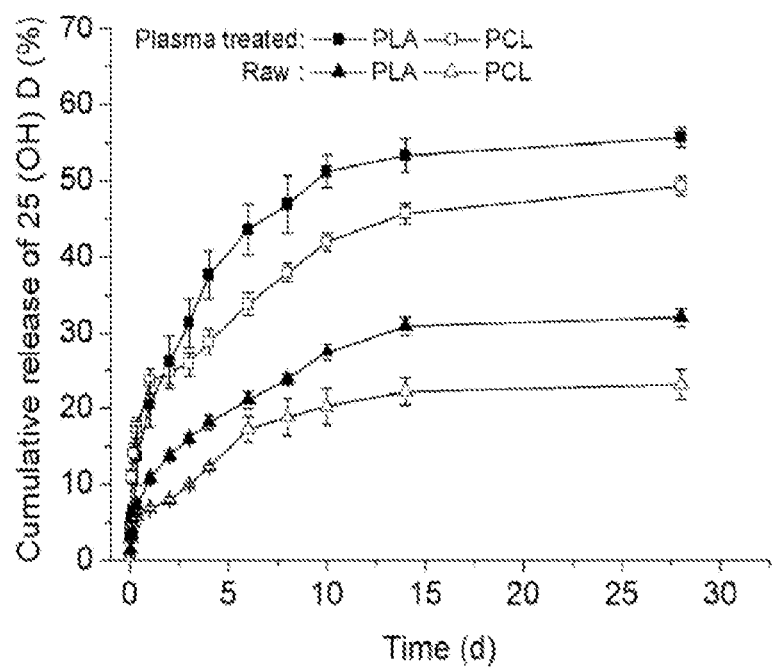

FIGS. 4A-4B include graphs showing the release profiles of 25(OH)D from various fiber samples, including a graph (FIG. 4A) showing the amount of 25(OH)D release and a graph (FIG. 4B) showing the cumulative percentage 25(OH)D release. Solid square (■): 25(OH)D loaded and air plasma treated PLA fibers. Open square (□): 25(OH)D loaded and air plasma treated PCL fibers. Solid triangle (▲): 25 (OH)D loaded PLA fibers, Open triangle (△): 25(OH)D loaded PCL fibers. Each data point represents arithmetic mean±SD values from three samples.

Figure 5A:
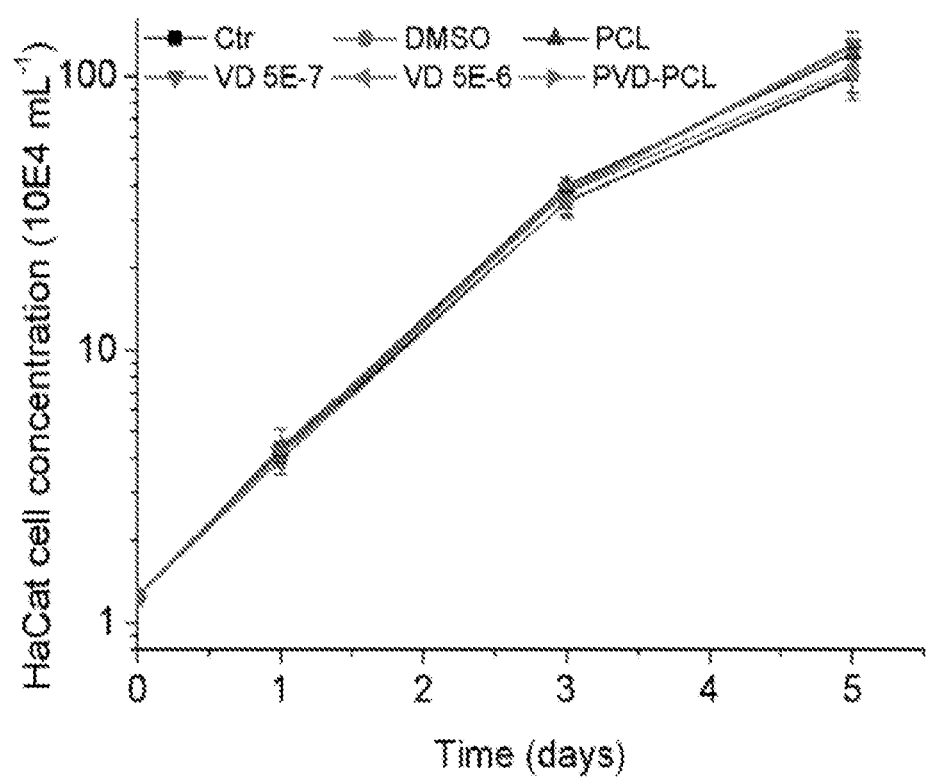
Figure 5B:
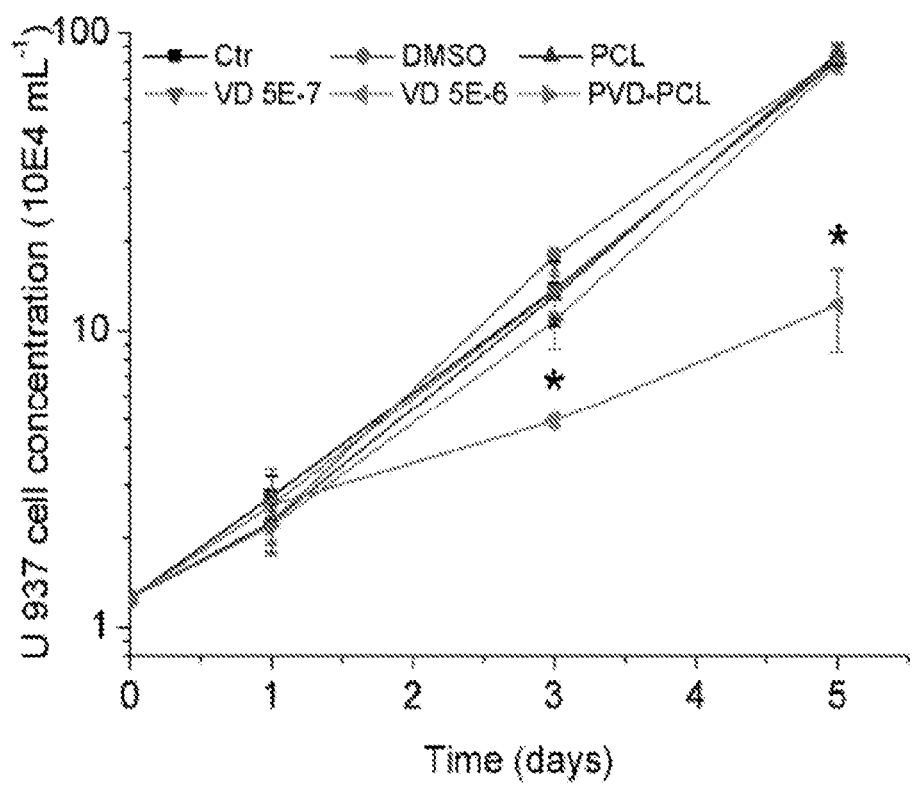

FIGS. 5A-5B include graphs showing the cytotoxicity of various formulations, including a graph showing HaCat (FIG. 5A) and a graph showing U937 (FIG. 5B) cell proliferation after treatment with 1 mg/ml PCL fibers, 0.52% DMSO, $5.0\times10^{-7}$M 25(OH)D, $5.0\times10^{-6}$M 25(OH)D, and 1 mg/ml plasma treated 25(OH)D loaded PCL fibers (containing $5.0\times10^{-7}$M 25(OH)D equivalent amount based on the calculations from release profiles in the first 3 days) for 1, 3 and 5 days. Each data point represents arithmetic mean±SD values from four samples. Statistical significance was calculated by student's t-test (*p<0.05).

Figure 6A:
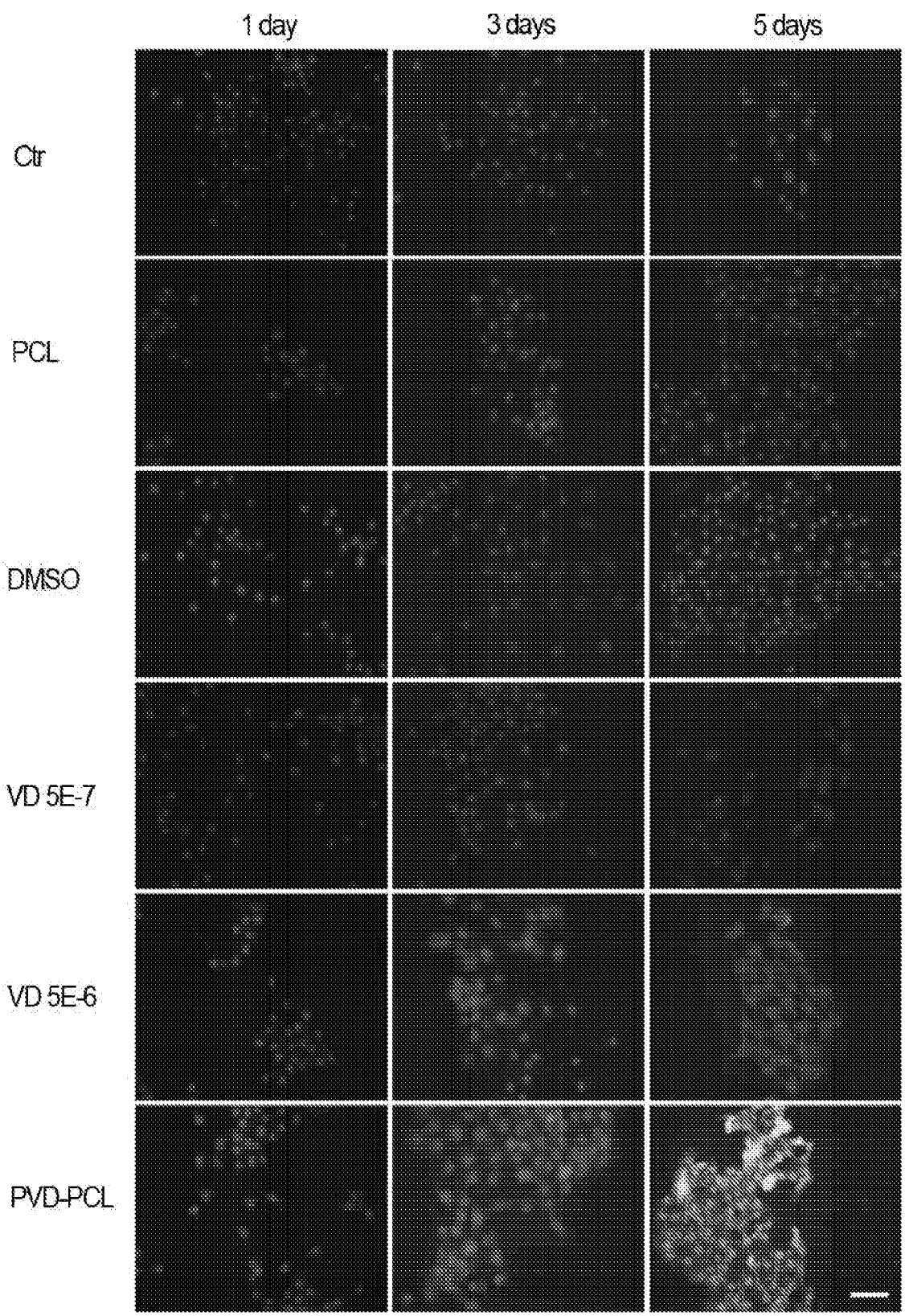
Figure 6B:
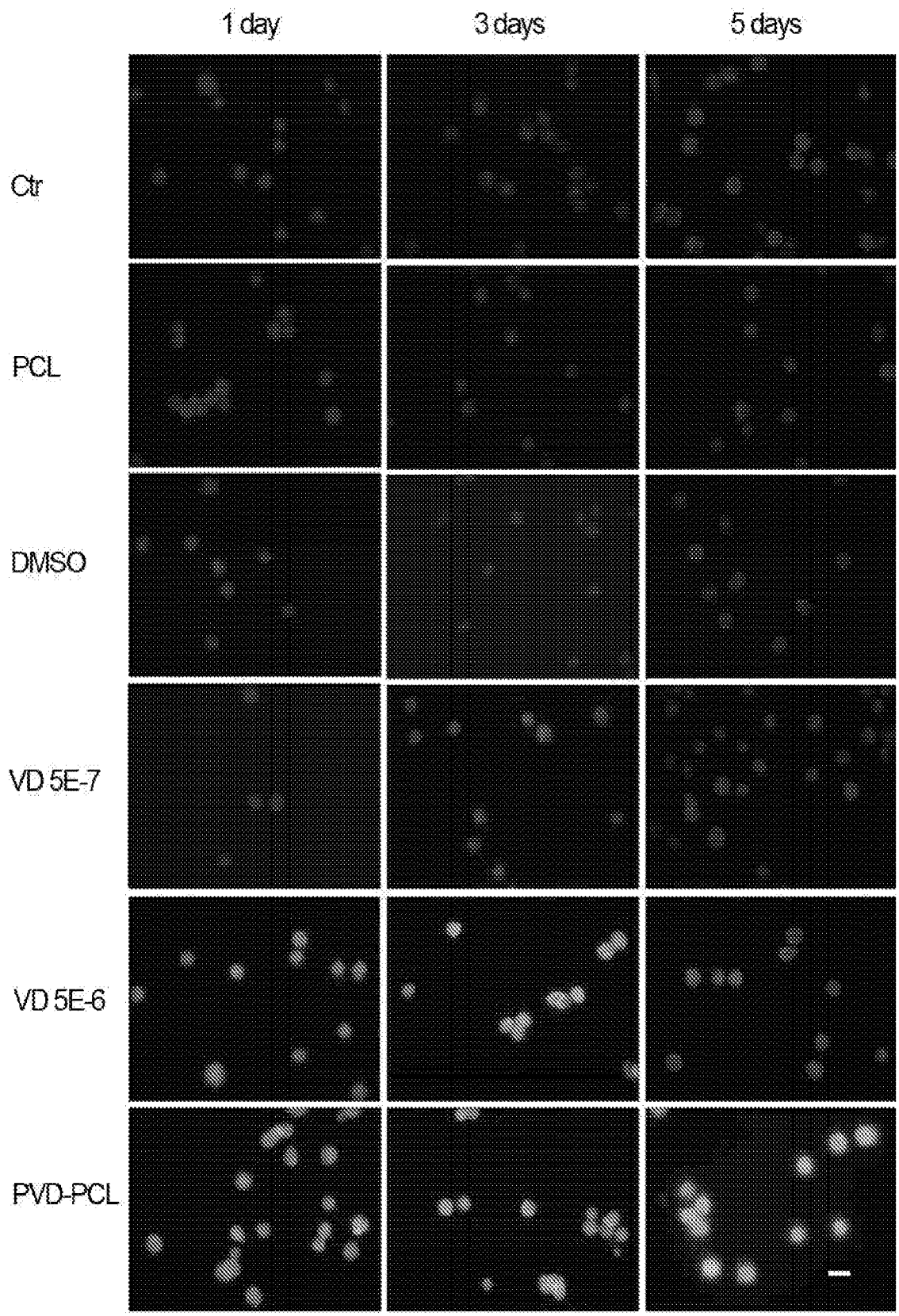

FIGS. 6A-6B includes images showing cathelicidin expression in HaCat (FIG. 6A) and U937 (FIG. 6B) cells after treatment with different formulations. Fluorescence microscopy images illustrate the cathelicidin expression of HaCat and U937 cells which were incubated in the presence of pristine 1 mg/ml PCL fibers, 0.52% DMSO, $5.0\times10^{-7}$M 25(OH)D, $5.0\times10^{-6}$ M 25(OH)D and 1 mg/ml plasma treated and 25(OH)D loaded PCL fibers (containing $5.0\times10^{-7}$ M 25(OH)D equivalent amount based on the calculations from release profiles in the first 3 days) for 1, 3 and 5 days. The expressed cathelicidin of cultured cells were stained with rabbit anti-cathelicidin antibody and mouse anti-rabbit FITC secondary antibody in green and the nuclei were counterstained with DAPI in blue. The scale bar is 20 µm.

Figure 7A:
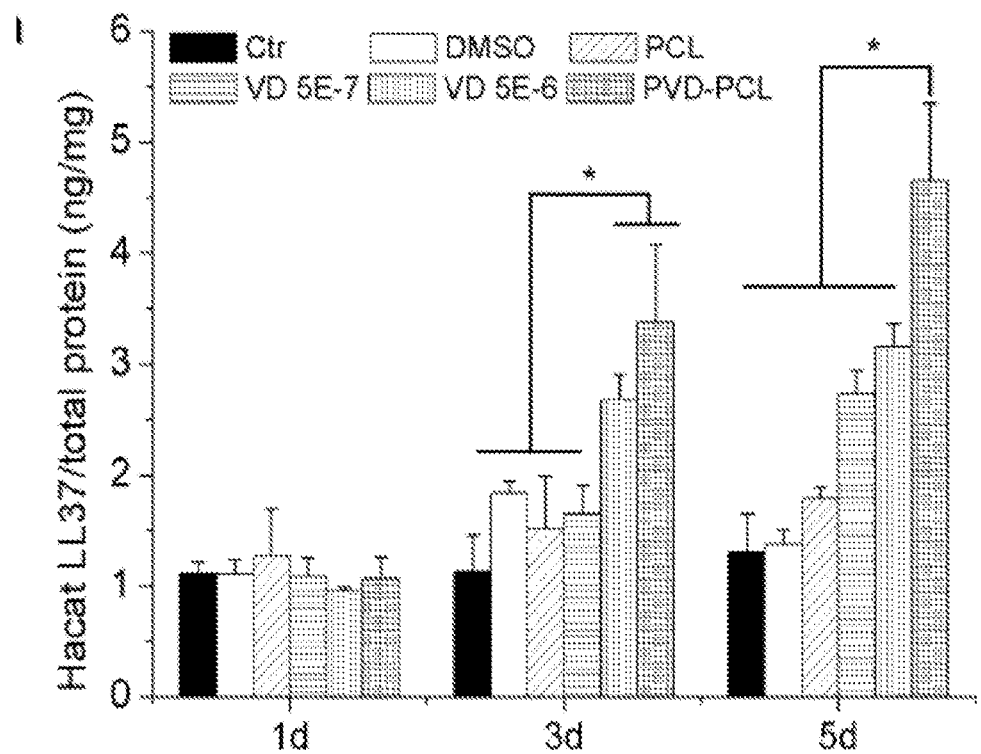
Figure 7B:
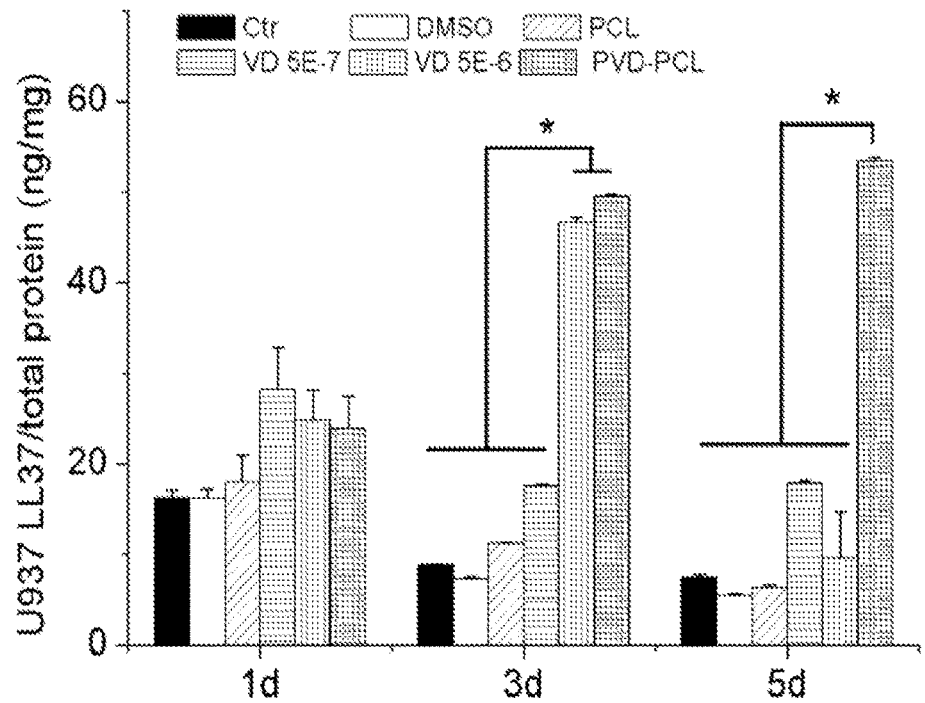

FIGS. 7A-7B include graphs showing the quantification of LL-37 expressed in HaCat (FIG. 7A) and U937 (FIG. 7B) cells after treatment with different formulations. Cells were incubated in the presence of 1 mg/ml pristine PCL fibers, 0.52% DMSO, $5.0\times10^{-7}$ M 25(OH)D, $5.0\times10^{-6}$ M 25(OH) D, and 1 mg/ml plasma treated and 25(OH)D loaded PCL fibers (containing $5.0\times10^{-7}$ M 25(OH)D equivalent amount based on the calculations from release profiles in the first 3 days) for 1, 3 and 5 days. Each data point represents arithmetic mean±SD values from three samples. Statistical significance was evaluated by student's t-test (*p<0.05).

Figure 8:
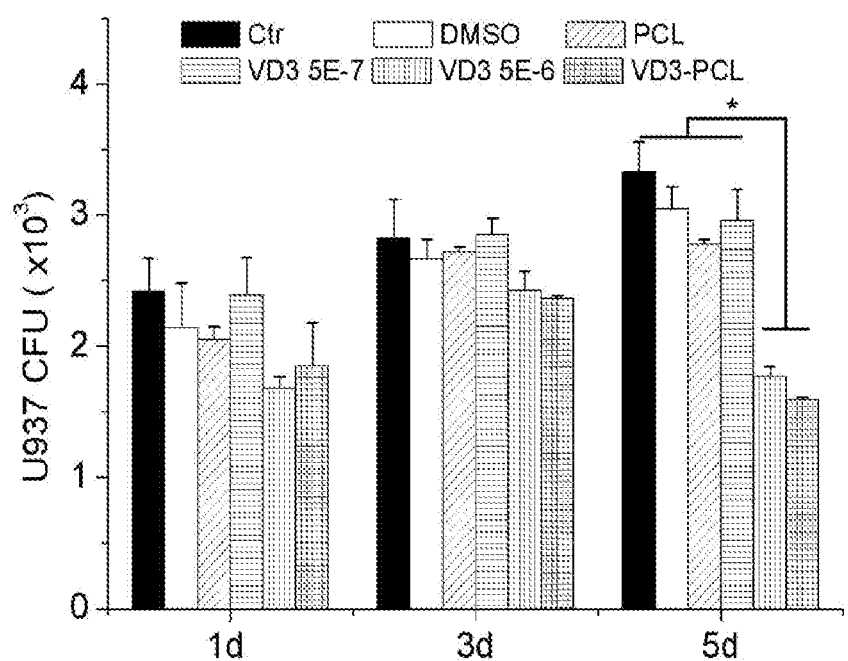

FIG. 8 is a graph showing the quantification of *Pseudomonas aeruginosa* CFUs treated by U937 lysis solutions. U937 were incubated in the presence of 1 mg/ml pristine PCL fibers, 0.52% DMSO, $5.0\times10^{-7}$ M 25(OH)D, $5.0\times10^{-6}$ M 25(OH)D, and 1 mg/ml plasma treated and 25(OH)D loaded PCL fibers (containing $5.0\times10^{-7}$M 25(OH)D equivalent amount based on the calculations from release profiles in the first 3 days) for 1, 3 and 5 days. Bacteria were incubated with cell lysis solutions and CFUs were counted on agar plates. Each data point represents arithmetic mean±SD values from three samples. Statistical significance was evaluated by student's t-test (*p<0.05).

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by one of ordinary skill in the art, definitions are set forth herein to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are described herein.

Following long-standing patent law convention, the terms "a", "an", and "the" refer to "one or more" when used in this application, including the claims. Thus, for example, reference to "a fiber" includes a plurality of such fiber, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed The presently-disclosed subject matter includes wound coverings and other compositions comprising vitamin D, or analogues or metabolites thereof. In some embodiments, the wound coverings include a substrate and vitamin D, or analogues or metabolites thereof, that are embedded in the substrate. In some instances, the compositions comprise a wound covering and the substrate can include one or more fibers. In this regard, in some embodiments the presently-disclosed subject matter includes wound coverings that include a substrate comprised of fibers that are embedded with vitamin D, or analogues or metabolites thereof.

As used herein, the term "wound covering" is inclusive of "wound bandages," "wound dressings," and other materials that are applied to treat a wound site. "Wound coverings" can be provided for temporary (e.g., 1 minute—several days) or more permanent (e.g., 1-3 months) treatment. In some embodiments a wound dressing includes a material that can be applied on or to a wound to treat the wound, and the wound dressing may or may not be in direct contact with a wound. Exemplary wound dressings include sterile pads, compresses, gauze, and the like. As discussed herein, in some embodiments, an exemplary wound dressing can include a substrate material that is comprised of a fibrous material (e.g., mesh). Moreover, "wound bandages" can be inclusive of materials used to fix a wound dressing on to a wound. In this regard, exemplary wound bandages include certain adhesive tapes, tie strips, compressive straps, and the like. Nevertheless, it should be understood that the terms wound dressing and wound bandage may be used interchangeably herein. Furthermore, in some instances a single wound covering may be classified as both a wound bandage and a wound dressing. The wound coverings described herein can also include novel wound coverings as well as commercially-available wound coverings capable of being utilized in accordance with the presently-disclosed subject matter.

In some embodiments of the presently-disclosed subject matter, the fiber substrates include a polymer, and in some embodiments the fiber substrates include a biodegradable polymer. In certain embodiments the nonbiodegradable or biodegradable fibers can include, but are not limited to poly(ε-caprolactone) (PCL), poly(lactide) (PLA), cellulose, and combinations thereof, wherein the fibers are embedded with vitamin D, or analogues or metabolites thereof.

In some embodiments, the present wound coverings and compositions can provide a sustained release of vitamin D, or analogues or metabolites thereof, and can therefore locally deliver vitamin D, or analogues or metabolites thereof, to a site that is on or within a subject. The release rates from embodiments of the present compositions can be tuned to minimize or eliminate the cytotoxic effects of vitamin D, or analogues or metabolites. On the other hand, direct administration of vitamin D, or analogues or metabolites thereof, can generate cytotoxicity and inhibition of cell growth at low concentrations ($10^{-7}$ M) (38-41). Furthermore, the presently-disclosed subject matter also includes methods for administering the present compositions to treat various diseases and conditions, including SSI and other local infections.

Embodiments of the present compositions utilize nanotechnology to address the problem of vitamin D metabolite delivery. Embodiments of the present compositions include biodegradable fiber-based wound coverings. Hydrogels provide soft-tissue like compliance but can be difficult to suture and too weak to support physiologic loads with difficulties in encapsulation of hydrophobic molecules. On the other hand, electrospun fibers provide materials for topical drug delivery, and permit the incorporation of hydrophobic molecules that can alter the release and degradation profiles by mediating the porosity of fibers. Accordingly, compared to traditional wound coverings, embodiments of the present fiber-based wound coverings have a number of advantages, such as haemostasis, high filtration, semi-permeability, conformability, and improved cosmesis/scar free.

As discussed herein, the presently-disclosed compositions include fibers that are embedded with vitamin D, or analogues or metabolites thereof. The term "vitamin D" as used herein refers to any one or more naturally occurring or synthetic analog of vitamin D as well as any metabolites of vitamin D. Thus, the term "vitamin D" is inclusive of analogues or metabolites thereof, unless expressly stated otherwise. Vitamin D can include any one or a combination of a group of fat-soluble prohormones, which encourage the absorption and metabolism of calcium and phosphorous. Five forms of vitamin D have been discovered, vitamin $D_1$ (complex of $D_2$ and lumisterol), $D_2$ (ergocalciferol), $D_3$ (cholecalciferol), $D_4$ (22-dihydroergocalciferol), $D_5$ (sitocalciferol). Vitamin D can also undergoes hydroxylation to become active, and, in this regard, the term "vitamin D" can specifically include 25-hydroxyvitamin $D_3$ (25(OH)D) or the like, and including man-made derivatives.

Vitamin D plays an active role in the immune system. Vitamin D is a secosteroid hormone that can be obtained through diet in the form of D2 (ergocalciferol, plant form) or D3 (cholecalciferol, animal form), with D3 more efficiently converted to the storage form 25-hydroxyvitamin D3 or 25(OH)D. Whether cutaneously produced or ingested, vitamin D3 is bound to Vitamin D Binding Protein (VDBP) and circulated throughout the body. Once vitamin D3 reaches the liver, hydroxylation by CYP27A1 occurs to form 25(OH)D. A second enzyme, CYP27B1, is found in over 30 cell types and acts to further metabolize 25(OH)D to form the locally produced intracrine $1.25(OH)_2D_3$ which is an active form of vitamin D. For the endocrine mechanism, vitamin D activation is in the proximal convoluted tubules of the kidneys where CYP27B1 is directly regulated by calcium and indirectly by PTH.

Active vitamin D plays a role in regulating transcription of approximately 3% of the human genome in over 30 different tissue types through vitamin D response elements (VDRE) on genes. Among its effects, vitamin D3 has been found to be an immune regulator with the ability to stimulate antimicrobial defense in epithelial barriers. Vitamin D's role in innate immunity begins with toll-like receptors (TLRs). Found on many white blood cells, the ability of these receptors to recognize certain pathogen associated molecular patterns (PAMPs) such as lipopolysaccharides and flagella allows the body to respond to pathogens regardless of prior exposure. Pathogen exposure can further result in increase in local $1.25(OH)_2D_3$ and VDR expression, creating an intracrine system that increases the oxidative burst potential of monocytes, recruits other immune cells to fight infection, and induces formation of natural antimicrobial peptides, such as cathelicidins and human defensins.

Protection against assault from microbial pathogens involves a complex series of skin, mucosal surface and immune cell interactions that produce antimicrobial peptides and proteins in response to specific stimuli. In macrophages and monocytes, antimicrobial peptide production by the vitamin D intracrine system is demonstrated by the production of hCAP18, a cathelicidin antimicrobial peptide (CAMP) precursor that is cleaved to release LL-37. A largely cationic peptide, LL-37 can act as an antibiotic by disrupting the membranes of microbes through its interaction with their negatively charged capsular polysaccharides. It also protects against symptoms of infection by neutralizing the feverproducing endotoxin of gram negative bacteria. By stimulating chemokine and cytokine production, LL-37 can recruit other cells to participate in immune responses. Intracellularly, CAMP is able to stimulate autophagy which allows macrophages and monocytes to destroy intracellular organelles, proteins, or phagocytosed bacteria. In addition to CAMP, 6 α-defensins and 4 β-defensins with anti-microbial properties are also induced by the 1.25(OH)D intracine system. Direct peptide application and over expression following gene therapy approaches have been precluded because of a number of significant toxicity issues.

Embodiments of the present compositions, by locally delivering vitamin D, or analogues or metabolites thereof, can therefore increase the local expression and secretion of LL-37 and other beneficial agents, including antimicrobial peptides, at or near the site of a composition. For instance, active 1.25(OH)$_2$D is synthesized in numerous extra-renal tissues (e.g. skin (basal keratinocytes, hair follicles), lymph nodes (granulomata), colon (epithelial cells and parasympathetic ganglia), pancreas (islets), adrenal medulla, brain (cerebellum and cerebral cortex), and placenta (decidual and trophoblastic cells)) and cells (e.g. keratinocytes, epithelia cells, neutrophils, monocytes, and macrophages) which express CYP27B1 and vitamin D receptor (VDR). The synthesized 1.25(OH)$_2$D bound to VDR can act as a transcription factor and lead to induction of hCAP 18. In its nascent form, hCAP 18 is inactive. Upon cleavage by proteinase 3, LL-37 is generated. Therefore, LL-37 can be derived from an inactive form (hCAP-18) produced in humans by various type of cells following exposure to active vitamin D, on analogues or metabolites thereof, (e.g., 1.25 (OH)$_2$D).

Secreted LL-37 and other beneficial agents can provide therapeutic benefits to a subject being treated. For instance, compositions administered on or near a surgical site can provide local expression of LL-37 at the surgical site, thereby providing a therapeutic approach to minimize the risk of surgical site infections (SSIs). In other embodiments the present compositions can be provided to treat microbial diseases or conditions.

When referring herein to vitamin D, or analogues or metabolites thereof, the terms "embedded" and "loaded" are used to refer to any means by which a substance is bound or loaded to a substrate, which is any material that can receive the substance. Embedded therefore includes any means by which vitamin D, or analogues or metabolites thereof, is bound to a substrate, such as a fiber substrate that is either natural or man-made. In some embodiments, fibers embedded with vitamin D are coated, soaked, and/or dipped with a solution containing vitamin D, and the vitamin D is found at the surface of the fibers and/or is absorbed within the fibers. In other embodiments, fibers embedded with vitamin D are polymerized and/or electrospun from a solution that includes vitamin D, and the vitamin D is present within the cured polymer fibers. As such, the terms "embedded" and "loaded" are inclusive of, but are not limited to, applying vitamin D, or analogues or metabolites thereof, to a substrate and/or making a substrate with vitamin D, or analogues or metabolites thereof. "Embedded" and "loaded" therefore refer an array of means by which vitamin D, or analogues or metabolites thereof, can be incorporated into substrates (e.g., fibers). In some embodiment, the terms include embedding commercially-available wound covers with vitamin D, or analogues or metabolites thereof.

The presently-disclosed compositions can include any concentration of vitamin D, or analogues or metabolites thereof, that may be sufficient for a particular application. The concentration of vitamin D, or analogues or metabolites thereof, that is sufficient can vary from subject to subject, depending on the species, age, and general condition of the subject, the severity of the condition being treated, the particular composition being used and its mode of administration, and the like. In some embodiments, the compositions include vitamin D, or analogues or metabolites thereof, at a concentration of about 1 mg/g to about 100 mg/g substrate. In certain embodiments the compositions include about 1 mg/g, 10 mg/g, 20 mg/g, 30 mg/g, 40 mg/g, 50 mg/g, 60 mg/g, 70 mg/g, 80 mg/g, 90 mg/g, or 100 mg/g of vitamin D, or analogues or metabolites thereof. Those of ordinary skill will recognize other concentrations of vitamin D, or analogues or metabolites thereof, that can be utilized in other embodiments upon reviewing this paper.

As described above, the compositions include fiber substrates. The one or more elongated fibers can include nanofibers and/or microfibers. In some embodiments, the fibers include a width of about 100 nm to about 10 um. In certain embodiments the fibers include a width of about 100 nm, 200 nm, 300 nm, 400 nm, 500 nm, 600 nm, 700 nm, 800 nm, 900 nm, 1000 nm, 1100 nm, 1200 nm, 1300 nm, 1400 nm, 1500 nm, 1600 nm, 1700 nm, 1800 nm, 1900 nm, or 2000 nm.

In some embodiments, the fibers are comprised of a polymer, and in some embodiments the fibers are comprised of electrospun polymers. In general, electrospinning is a process whereby an electric field is applied between a nozzle (e.g, capillary, syringe, etc.) containing a polymer and a conducting substrate. As the polymer is ejected from the nozzle, it cures as it is pulled towards the substrate. In this manner, the polymer can be ejected from the nozzle to form a fiber. Those of ordinary skill in the art upon reviewing this paper will appreciate specific electrospinning methods for making the presently-disclosed fibers.

The polymer is not particularly-limited. In some embodiments, the polymer is biocompatible. In other embodiments the polymer is biodegradable. In some embodiments, the polymer includes PCL and/or PLA, which are biocompatible and biodegradable polymers that have been approved by the U.S. Food and Drug Administration (FDA) for certain human clinical applications (27,28). In other embodiments, the polymers include cellulose (e.g., cotton).

The term "biocompatible" as used herein, is intended to describe a characteristic of compositions that do not typically induce undesirable or adverse side effects when administered in vivo. For example, biocompatible compositions may not induce side effects such as significant inflammation and/or acute rejection. It will be recognized that "biocompatibility" is a relative term, and some side effects can be expected even for some compositions that are biocompatible. In some embodiments, a biocompatible compositions does not induce irreversible side effects, and in some embodiments a compositions is biocompatible if it does not induce long term side effects. One test to determine biocompatibility is to measure whether cells die upon being exposed a material in vitro. For instance, a biocompatible compositions may cause less than about 30%, 20%, 10%, or 5% cell death.

The term "biodegradable" as used herein describes a characteristic of compositions that degrade under physiological conditions to form a product that can be metabolized or excreted without damage to the subject. In certain embodiments, the compositions is metabolized or excreted without permanent damage to the subject. Biodegradable compositions can be hydrolytically degradable, can require cellular and/or enzymatic action to fully degrade, or both.

Biodegradable compositions also include materials that are broken down within cells. Degradation may occur by hydrolysis, oxidation, enzymatic processes, phagocytosis, or other processes.

Degradation rates can vary, and may be on the order of hours, days, weeks, months, or years. Factors that affect degradation rate include fiber (polymer) composition and water penetration into the fibers. In some embodiments, the present fibers degrade under physiological conditions (e.g., 10-50° C., pH 4-10) in about 1 day to about 100 days, in about 1 day to about 50 days, or in about 1 day to about 30 days. Embodiments thus include fibers that can degrade under physiological conditions in about 10 days, 20 days, 30 days, 40 days, 50 days, 60 days, 70 days, or 90 days. Furthermore, the degradation rates of fiber materials can be tubed by incorporation of certain enzymes, such as proteinase K and lipase. As discussed below, the degradation rates of the fibers can be tuned to also tune the rate of release of vitamin D, or analogues or metabolites thereof, from the fibers.

The vitamin D, or analogues or metabolites thereof, can be released at sustainable rates from the present compositions. A release is "sustainable" if it is released over the course of one or more days, rather than being released as a burst at one time point. The release rate of vitamin D, or analogues or metabolites thereof, is determined by rate of fiber (polymer) degradation, water penetration, dissolution and diffusion of embedded agents, and the like. Thus, fibers that degrade in about 1 to about 50 days can release vitamin D, or analogues or metabolites thereof, over a portion or all the 1 to 50 day time period that the fibers degrade. Water penetration into fibers can also accelerate the release of vitamin D, or analogues or metabolites thereof, and can cause rate of release to exceed the degradation rate of the fibers. Such water penetration can be affected by the structure (e.g., porosity), the hydrophobicity, and the wettability of the fibers. In addition, increasing hydrophilicity and wettability of fibers may enhance the absorption of wound exudate.

In this respect, in some embodiments, the fibers are subjected to a plasma treatment process to alter the hydrophobicity of the fibers. In some embodiments, plasma treatment can increase the hydrophobicity of a fiber, potentially decreasing the rate of release of vitamin D, or analogues or metabolites thereof, from the fibers. In other embodiments, plasma treatment can increase the hydrophilicity of a fiber, potentially increasing the rate of release of vitamin D, or analogues or metabolites thereof, from the fibers.

Those of ordinary skill upon reviewing this paper will appreciate that the present wound coverings and compositions can include a variety of substrates that are embedded with vitamin D, or analogues or metabolites thereof. The fiber-based compositions described herein comprise one embodiments of the presently-disclosed subject matter. In other embodiments the substrates are selected from both known and novel medical devices, sutures, other wound coverings (e.g., bandages), and the like that are embedded with vitamin D, or analogues or metabolites thereof.

The presently-disclosed subject matter also includes methods for treating a subject. In some embodiments the treating includes minimizing the risk of, reducing, or eliminating a microbial disease or condition in a subject. In some embodiments, the fibers of a composition are formed into a mesh. Furthermore, in some embodiments the fibers can be oriented to form a flat membrane. Fibers in the form of a mesh or membrane can then be applied as a wound covering. In some instances, the wound covering can be applied as a membrane over a tissue injury or wound either topically or within a subject. In some embodiments, the sites therefore may include cuts, scrapes, and other wounds on a subject. Wound coverings can also be applied to a surgical site. After administration, the fibers locally release a dose of the vitamin D, or analogues or metabolites thereof. In some instances, such local delivery from a surgical site can help minimize the risk of developing surgical site infections.

The terms "treatment" or "treating" are thus used herein to refer to the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative (prophylactic) treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "subject" as used herein is inclusive of both human and animal subjects. The presently-disclosed subject matter provides compositions for delivering vitamin D, or analogues or metabolites thereof, to mammals such as humans, as well as those mammals of importance due to being endangered, such as Siberian tigers; of economic importance, such as animals raised on farms for consumption by humans; and/or animals of social importance to humans, such as animals kept as pets or in zoos. Other animals include, but are not limited to, carnivores such as cats and dogs; swine, including pigs, hogs, and wild boars; ruminants and/or ungulates such as cattle, oxen, sheep, giraffes, deer, goats, bison, camels; horses, birds. Thus, veterinary uses are provided in accordance with the presently-disclosed subject matter.

The presently-disclosed subject matter is further illustrated by the following specific, but non-limiting, examples set forth below. The examples may include compilations of data that are representative of data gathered at various times during the course of development and experimentation related to the presently-disclosed subject matter.

EXAMPLES

Example 1

This Example describes the production and morphological characterization of embodiments of 25-hydroxyvitamin $D_3$ (25(OH)D) loaded fibers. 25-hydroxyvitamin $D_3$ (25 (OH)D) and mouse anti-goat IgG-fluorescein isothiocyanate (FITC) were purchased from Santa Cruz biotechnology, Inc. (Dallas, Tex., USA). Goat anti-cathelicidin polyclonal antibody was purchased from Abcam (Cambridge, Mass. USA). Protease inhibitor cocktail, PCL (Mw=70~90 kDa) and PLA (Mw=103~259 kDa) were bought from Sigma-Aldrich (St. Louis, Mo., USA). Trypsin-EDTA, Dulbecco's Modified Eagle Media and Roswell Park Memorial Institute (RPMI) 1640, 4',6-diamidino-2-phenylindole (DAPI) were bought from Invitrogen (Grand Island, N.Y., USA). Triton-X100, M-PER mammalian protein extraction reagent, dichloromethane (DCM), N, N-dimethylformamide (DMF), dimethylsulfoxide (DMSO) and fetal calf serum (FBS), MicroBCA kit were acquired from Thermo fisher scientific (Waltham, Mass., USA). 25(OH)D and LL-37 enzyme-linked immunosorbent assay (ELISA) kits were purchased from Diagnostika Gmbh (Hamburg, Germany) and Hycult biotech (Plymouth Meeting, Pa. USA) respectively.

Poly($\varepsilon$-caprolactone) (PCL) and poly($_L$-lactide) (PLA) fibers with and without 25(OH)D loading were produced using electrospinning (see, e.g., 29-31). PCL and PLA were selected as model materials because they are biocompatible and biodegradable polymers and have been approved by FDA for certain human clinical applications. PCL or PLA was dissolved in a solvent mixture consisting of DCM and DMF with a ratio of 4:1 (v/v) at a concentration of 10% (PCL) or 4% (PLA) (w/v). The stock solution of 25(OH)D was prepared by dissolving 1 mg 25(OH)D in 1 ml DMSO and was added to the polymer (VD-PCL or VD-PLA) solution with an initial drug loading of 1 mg/g. Polymer solutions were pumped at a flow rate of 0.5 ml/h using a syringe pump, while a potential of 12 kV was applied between the spinneret (a 22-gage needle) and a grounded collector located 12 cm apart from the spinneret. A rotating drum was used to collect membranes composed of random fibers with a rotating speed less than 100 rpm. The fiber mats were then treated with air plasma (PVD-PCL and PVD-PLA) using a plasma cleaner (PDC-32G, Harrick Plasma, Ithaca, N.Y.) for 8 min at a medium setting. All the fiber samples were treated by air plasma and sterilized by y radiation at a dose of 15 kGy prior to use for cell culture.

The morphology and diameter of fiber samples were characterized by a SEM (FEI, Quanta 200, Oregon, USA) and by AFM (Bruker surface metrology division, Goleta, USA). To avoid charging, polymeric fiber samples were fixed on a metallic stud with double-sided conductive tape and coated with platinum for 4 min in vacuum at a current intensity of 10 mA using a sputter coater. SEM images were acquired at an accelerating voltage of 30 kV. The AFM images were obtained in ScanAsyst (peak force) mode by scanning the fibers deposited on the cover glass surface under ambient conditions using a Bruker Catalyst with a NanoScope V Controller. Sharp silicon probes (ScanAsyst air, k~0.4 N/m, Bruker) were used to collect the images with the parameter settings as below: 512×512 pixels resolution, typical scanning rate 1.5 Hz. The brightness of features in captured topographic images increases as a function of height of the samples.

FIGS. 1A-1D show scanning electron microscopy (SEM) images of the morphology of PCL fibers, VD-PCL fibers, PLA fibers and VD-PLA fibers. The diameters of PCL fibers, VD-PCL fibers, PLA fibers and VD-PLA fibers were 633±296 nm, 906±446 nm, 708±156 nm, and 1204±397 nm, respectively. The surface of PCL fibers was smooth and remained almost the same after encapsulation of 25(OH)D. In contrast, PLA fibers showed some wrinkles on the surface and more wrinkles were observed on the surface after encapsulation. In addition, the PCL and VD-PCL fibers were cylindrical in shape, while PLA and VD-PLA fibers were shaped like a ribbon.

The morphology of fibers was further characterized using atomic force microscopy (AFM), as shown in FIGS. 2A-2D. It was observed that the surface of the PCL fibers was smooth and similar to that of VD-PCL fibers. However, the surface of VD-PLA fibers seemed rougher than PLA fibers. There were no morphological changes in the fibers after plasma treatment (FIGS. 3A-3D).

For the Examples described herein, three replicates were tested for each data point. The statistical analysis was performed on the means of the data obtained from at least three independent experiments. All the results were presented as means and the significance was assessed using student's t-test. p values of 0.05 or less among the groups were considered to be significant and very significant.

Example 2

This Example describes the in vitro release and drug loading characteristics of the fibers produced in Example 1. The in vitro release of 25(OH)D from the fibers was evaluated by immersing 10 mg fiber samples in the 10 ml PBS solution at 37° C. The supernatants were collected at each time point and replaced by fresh PBS solutions. Drug loading and encapsulation efficiency were determined by dissolving approximately 10 mg fiber samples in 0.2 ml glacial acetic acid. Then, the 25(OH)D concentrations of all collected samples were determined by using a 25(OH)D ELISA kit according to the manufacturer's instructions.

The drug loading and encapsulation efficiency for VD-PCL were 0.76% and 76±7.4% while the corresponding values for VD-PLA fibers were 0.90% and 90±5.4%. FIGS. 4A-4D show the in vitro release profiles of raw fibers (VD-PCL and VD-PLA) and plasma treated fiber formulations (PVD-PCL and PVD-PLA). FIG. 4A shows the amount of 25(OH)D released from each sample over 28 days. Greater amounts of 25(OH)D were released from PLA fiber samples than from PCL fiber samples with plasma treatment increasing the release in both fiber formulations (289 ng vs 502 ng for VD-PLA vs PVD-PLA and 177 ng vs 378 ng for VD-PCL vs PVD-PCL). FIG. 4B demonstrates that the cumulative percentage of released 25(OH)D from PLA fibers were greater than PCL fibers with plasma treatment increasing the release (32% vs 55% for VD-PLA vs PVD-PLA and 23% vs 49% for VD-PCL vs PVD-PCL).

Example 3

This Example describes cell proliferation of cells treated with the PCL fibers produced in Example 1. Human keratinocyte cell line (HaCat) and monocyte cell line (U937) were cultured in D-MEM with 10% FCS and RPMI-1640 media with 10% FCS respectively. The cultures were maintained at 37° C. under 95% air and 5% $CO_2$ until reaching 80% confluence. The subconfluent HaCat cells were dissociated with a 0.05% trypsin-EDTA and re-suspended in a fresh complete media. U937 cells were precipitated by 300 g centrifugation and then re-suspended in a fresh complete media. The single HaCat cell suspensions were created by gently pipetting up and down HaCat cell aggregates and then placed in 6-cm culture dishes and incubated for 1 day. At the beginning of experiments, $5.0 \times 10^5$, $2.0 \times 10^5$ and $1.0 \times 10^5$ cells were seeded in the culture dishes for 1-day, 3-day, and 5-day treatments, respectively. The media was then replaced by D-MEM containing 0.52% DMSO, D-MEM containing $5.0 \times 10^{-7}$ M 25(OH)D, D-MEM containing $5.0 \times 10^{-6}$ M 25(OH)D, D-MEM containing 1 mg/ml pristine PCL fibers, and D-MEM containing 1 mg/ml 25(OH)D loaded PCL fibers and incubated for 1, 3, and 5 days. Of note, $5.0 \times 10^{-6}$ M 25(OH)D was chosen as a control due to cytotoxicity in OKF6-TERT2 cells. The single U937 cell suspension was placed in 6-cm culture dishes. Then, the cultures were incubated with RPMI-1640, RPMI-1640 containing 0.52% DMSO, RPMI-1640 containing 1 mg/ml pristine PCL fibers, RPMI-1640 containing $5.0 \times 10^{-7}$M 25(OH)D, RPMI-1640 containing $5.0 \times 10^{-6}$ M 25(OH)D, and RPMI-1640 containing 1 mg/ml 25(OH)D loaded PCL fibers for 1, 3, and 5 days. Biological characterization was first performed with PCL fibers, rather than PLA fibers.

The HaCat cells and U937 cells were seeded in 24-well plates. Each well contained $2.5 \times 10^4$ cells and 1 ml culture media (D-MEM for HaCat and RPMI-1640 for U937). The cells were treated following the procedure described in the section of cell culture and treatments. The subconfluent HaCat cells were harvested at day 1, 3, and 5 with 0.05% trypsin-EDTA solution and re-suspended in fresh complete media. U937 cells were re-suspended by gently pipetting up and down. The cell density was calculated based on the cell counting (FIGS. 5A-5B).

Both keratinocytes and monocytes are present and involved in the wound healing process and possess the machinery to process vitamin D and generate antimicrobial peptides. According to 25(OH)D release profiles, cumulatively released 25(OH)D from 1 mg PVD-PCL fibers was approximately 190 ng and 230 ng in the first 3 and 5 days, respectively. Therefore, the equivalent concentration of 25(OH)D for 1 mg PVD-PCL fibers in 1 ml media in the first 3 days was approximately $5.0 \times 10^{-7}$ M. The treatment of $5.0 \times 10^{-7}$ M 25(OH)D free drug was conducted as a control with a 10-fold increase in 25(OH)D concentration used as an additional toxicity control ($5.0 \times 10^{-6}$ M). Since 1 mg/ml 25(OH)D stock solution was prepared in DMSO, 0.52% DMSO (v/v) was added into complete culture media as a solvent control group. Air plasma treated PCL fibers without drug loading was employed as another control group. FIG. 5A shows the change of cell concentrations along with incubation times after treatment with different formulations. There were no significant differences of HaCat concentration/proliferation after treatment with various experimental groups at each time point, suggesting no evident cytotoxic effect on HaCat cells. However, a slight decrease in the proliferation rate was found for all experimental groups after 3 days' incubation, which could be due to the exhaustion of nutrients in the culture media. In contrast, the same treatments on U937 cells showed one notable difference: the proliferation rate of U937 cells reduced dramatically after treatment of $5.0 \times 10^{-6}$ M 25(OH)D for 3 days and 5 days, exhibiting its cytotoxic effects (FIG. 5B). Except for $5.0 \times 10^{-6}$ M 25(OH)D, all other treatment groups showed marginal effects on the proliferation/concentration of U937 cells, indicating no cytotoxicity to the cells.

Example 4

This Example describes an immunofluorescence assay performed on cells treated with the PCL produced in Example 1. The cells were treated with different formulations as discussed above, the cells were rinsed with PBS twice and fixed with 4% paraformaldehyde for 30 min at 37° C. followed by incubation with TNBS (0.05% Triton-X100, 2% FBS in pH 7.2 PBS) for 30 minutes at room temperature prior to immunostaining. Goat anti-cathelicidin polyclonal antibody (1:200) was incubated to label intercellular cathelicidin at 4° C. overnight. Both the full length and cleaved C terminus of cathelicidin (hCAP18) were labeled. Mouse anti-goat IgG-FITC antibody (1:100) was incubated for 2 h after removal of primary antibody and washed with TNBS three times. Then, the secondary antibody was removed and washed by TNBS three times. Nuclei were counterstained with 10 μM DAPI in blue. Images were taken with a digital camera (Carl Zeiss). The exposure time for taking images for HaCat and U937 cells was fixed at 400 ms and 40 ms, respectively.

No hCAP 18 expression was seen in PCL and DMSO controls. There was positive green fluorescent staining for hCAP 18 in HaCat cells after 3 days treatment of $5.0 \times 10^{-6}$ M 25(OH)D or incubation with PVD-PCL which provided approximately $5.0 \times 10^{-7}$ M 25(OH)D (FIG. 6A). The intensity of green fluorescence increased from day 3 to day 5. The $5.0 \times 10^{-7}$ M 25(OH)D control did not demonstrate hCAP 18 expression. As shown in FIG. 6B, U937 cells were treated with pristine PCL fibers, DMSO, or $5.0 \times 10^{-7}$ M 25 (OH)D showed negative staining of cathelicidin at each time point. By contrast, U937 cells exhibited expression of hCAP 18 after one day's treatment of $5.0 \times 10^{-6}$ M 25(OH)D or PVD-PCL fibers containing approximately $5.0 \times 10^{-7}$ M 25(OH)D (equivalent amount based on the calculations from release profiles in the first 3 days). With increasing incubation time, the fluorescence intensity of U937 cells increased after treatment of $5.0 \times 10^{-6}$ M 25(OH)D while maintained the similar level when treated with PVD-PCL fibers for 3 days. The fluorescence intensity (expression level of hCAP 18) of U937 cells decreased after treatment of $5.0 \times 10^{-6}$ M 25(OH)D from day 3 to day 5; however, the fluorescence intensity (expression level of hCAP 18) of U937 cells sharply increased when treated with PVD-PCL fibers within the same culture period. The cell proliferation assays demonstrated a decrease in cell concentration on days 3 and 5 for the U937 cells treated with $5.0 \times 10^{-6}$ M 25(OH)D.

Example 5

This Example describes the production of LL-37 in cells treated with the PCL fibers produced in Example 1. Single cell suspensions of both HaCat cells (human keratinocyte cell line) and U937 cells (leukemic monocyte lymphoma cell line) were seeded in 6-cm culture dishes. $5.0 \times 10^5$, $2.0 \times 10^5$ and $1.0 \times 10^5$ cells were seeded in the culture dishes for 1-day, 3-day, and 5-day treatments, respectively. Cells were treated with different formulations as described above and harvested at each time point. The subconfluent HaCat cells and U937 cell suspensions were washed with PBS twice. Subsequently, 300 μl of the M-PER mammalian protein extraction reagent with 0.1% protease inhibitor cocktail was added to the extraction reagent. They were agitated for 20 min and lysate was collected and transferred to a 1.5-ml microcentrifuge tube. The samples were centrifuged at 14000×g for 40 min at 4° C. to pelletize the cell debris and the supernatant was transferred to a new tube for analysis. Total protein concentration was tested by MicroBCA kit before ELISA test. Concentrations of LL-37 in cell lysate were determined by LL-37 ELISA assay kit based on the manufacturer's instructions.

It was observed that the LL-37 production in both HaCat cells and U937 cells was significantly higher when incubated with PVD-PCL fibers than the free drug for 3 and 5 days (FIGS. 7A-7B). The amount of LL-37 produced from U937 cells increased when treated with $5.0 \times 10^{-6}$ M 25(OH)D for 3 days and then decreased sharply after 5 days incubation. This result was in line with the data of hCAP18 expression. Importantly, both HaCat and U937 cells were treated with plasma treated and 25(OH)D loaded PCL fibers had a stable production of high amounts of LL-37. Most interestingly, the cells treated with plasma treated and 25(OH)D loaded PCL fibers containing approximately $5.0 \times 10^{-7}$ M 25(OH)D (equivalent amount based on the calculations from release profiles in the first 3 days) can produce higher amount of LL-37 than the cells treated with $5.0\times10^{-6}$ M 25(OH)D—10.3 and 8.3 times concentrations of plasma treated and 25(OH)D loaded PCL fiber group after incubation for 3 and 5 days consistent with the results from cell proliferation and immunofluorescent assays. In addition, it is worth noting that U937 cells can produce a 10-fold larger amount of LL-37 than HaCat cells under the same testing conditions.

Example 6

This Example describes the antibacterial activities in cells treated with the PCL fibers produced in Example 1. Briefly, bacteria were incubated with cell lysis solutions and CFUs were counted on agar plates. The numbers of CFUs showed no significant difference between the lysis solutions of U937 cells that were treated with different formulations for 1 day and 3 days. In contrast, the lysis solutions of cells which were treated with $5.0\times10^{-6}$ M 25(OH)D and plasma treated and 25(OH)D loaded PCL fibers for 5 days showed significantly lower numbers of CFUs than other treatment groups (FIG. 8).

Discussion of Examples 1-6

Surgical site infections continue to represent a significant portion of healthcare-associated infections. Antibiotic resistance in common pathogens reinforces the need to minimize surgical site infections. Recent studies showed the synthesis of active 1,25-hydroxyvitamin $D_3$ occurred in numerous extrarenal sites in cells such as keratinocytes, epithelia cells, neutrophils, monocytes and macrophages which express CYP27B1 and vitamin D receptor. The synthesized 1,25-hydroxyvitamin $D_3$ bound to vitamin D receptor acting as a transcription factor leading to induction of hCAP 18. In its nascent form, hCAP 18 is inactive. Upon cleavage by proteinase 3, LL-37 is generated. Therefore, LL-37 can be derived from an inactive form (hCAP-18) produced in humans by various type of cells following exposure to active 1,25-hydroxyvitamin $D_3$ with local production dependent on the storage form of 25-hydroxyvitamin $D_3$. LL-37 acts as an antibiotic by disrupting the membrane of microbes exhibiting broad-spectrum microbicidal activity against bacteria, fungi, and viruses. Direct peptide application and over expression following gene therapy approaches have been precluded because of a number of significant toxicity issues. Additionally, direct administration of 1,25-hydroxyvitamin $D_3$ does induce hCAP 18 expression but low concentrations ($10^{-7}$ M 1,25-hydroxyvitamin $D_3$) generate cytotoxicity and led to the inhibition of cell growth. Other strategies are therefore needed to improve hCAP 18 expressions and LL-37 productions. A recent study showed that administration of 25-hydroxyvitamin $D_3$ resulted in an increase of cathelicidin expression in wounds by activation of CYP27B1. It has been demonstrated that 25-hydroxyvitamin $D_3$ can enhance innate immunity by inducing a number of cells including keratinocytes, neutrophils, monocytes, macrophages, and epithelial cells which have vitamin D receptor to produce antimicrobial peptides LL-37. In this study, electrospun PLA and PCL fibers were developed as a wound dressing for local sustained delivery of 25-hydroxyvitamin $D_3$ a circulation form of vitamin $D_3$ to induce antimicrobial peptide production. Biological effects were demonstrated in plasma-treated and 25-hydroxyvitamin $D_3$ loaded PCL fibers with increased production of hCAP 18 and LL-37 in HaCat and U937 cells.

Both PLA and PCL fibers are were able to encapsulate and deliver 25-hydroxyvitamin $D_3$ in a sustained manner. The rough surface and ribbon shape of PLA fibers could be due to the high molecular weight and slow diffusion in the solvent of PLA molecules. In contrast, low molecular weight and fast diffusion in the solvent of PCL molecules led to the smooth surface and cylindrical shape of PCL fibers. The in vitro release rate of 25-hydroxyvitamin $D_3$ from PLA and PCL fibers is mainly determined by the rate of polymeric fiber degradation, water penetration, dissolution and diffusion of encapsulated 25-hydroxyvitamin $D_3$. In vitro release results show that 25-hydroxyvitamin $D_3$ released faster from PLA fibers than from PCL fibers, which could be partly attributed to better hydrophilicity of PLA fibers compared to PCL fibers. Plasma treatment can significantly improve the hydrophilicity and wettability of fibers as water contact angles changed from 150° prior to treatment to 0° after treatment, which could lead to fast water penetration and release rate (FIGS. 3A-3D). The foregoing study demonstrated that the air plasma treatment enhanced the release rate of 25-hydroxyvitamin $D_3$ from PLA and PCL fibers. The fiber degradation may have little impact on the release rate of 25-hydroxyvitamin $D_3$ as both PLA and PCL fibers degraded slowly. Previous studies demonstrated PLA fibers had significant swelling after incubation for 4 weeks. The swelling of PLA fibers may enlarge the pore size in fibers and thus enhance the rate of water penetration and diffusion of 25-hydroxyvitamin $D_3$, eventually resulting in a faster release rate. Therefore, the swelling effect could partially contribute to the faster release rate of 25-hydroxyvitamin $D_3$ from PLA fibers compared to PCL fibers. The release profiles of 25-hydroxyvitamin $D_3$ can be further tailored through modulation of degradation rates of fiber materials as the degradation rates of PCL and PLA fibers can be controlled by incorporation of certain enzymes like proteinase K and lipase. In addition, the improvement of hydrophilicity and wettability of fibers may enhance the absorption of wound exudate. So, it is, in some instances, beneficial to treat 25-hydroxyvitamin $D_3$ loaded PCL and PLA fibers with air plasma. Considering the cost reduction in practical applications, 25-hydroxyvitamin $D_3$ loaded PCL fibers were chosen to conduct the biological tests because of higher cost of PLA than PCL raw materials.

HaCat cells and U937 cells are human keratinocytes and monocytes, respectively. Both types of cells express CYP27B1 and vitamin D receptor that are essential for the production of hCAP 18 a cathelicidin anti-microbial protein containing the antibacterial peptide LL-37. The foregoing studies demonstrated that HaCat cells incubated with plasma treated and 25-hydroxyvitamin $D_3$ loaded PCL fibers containing approximately $5.0\times10^{-7}$ M 25-hydroxyvitamin $D_3$ can express higher level of hCAP 18 and LL-37 compared to the cells administered by $5.0\times10^{-6}$ M 25-hydroxyvitamin $D_3$ for 5 days with no effects on cytotoxicity. Even though the released 25-hydroxyvitamin $D_3$ from plasma treated and 25-hydroxyvitamin $D_3$ loaded PCL fibers was much lower than exogenous administered 25-hydroxyvitamin $D_3$, it was equally effective at LL-37 production indicating a biological advantage of sustained release fiber formulations. The above-described results also showed that the expression of hCAP 18 and LL-37 of keratinocytes increased after incubation with $5.0\times10^{-6}$ M 25-hydroxyvitamin $D_3$ from day 1 to 5. In addition, $5.0\times10^{-6}$ M 25-hydroxyvitamin $D_3$ free drug showed marginal cytotoxic effects on the HaCat cells, which is in accordance with previous studies. In contrast, the expression of hCAP 18 and LL-37 of U937 cells after administration of $5.0\times10^{-6}$ M 25-hydroxyvitamin $D_3$ increased from day 1 to 3 and decreased from day 3 to 5. When incubated with plasma treated and 25-hydroxyvitamin $D_3$ loaded PCL fibers containing approximately $5.0 \times 10^{-7}$ M 25-hydroxyvitamin $D_3$, the expression of hCAP 18 and LL-37 of U937 cells kept increasing from day 1 to 5 with a 10-fold increase in LL-37 production over HaCaT cells FIGS. 7A-7B). Importantly, compared to administration of $5.0 \times 10^{-6}$ M free drug, U937 cells expressed similar levels of hCAP 18 and LL-37 after incubation with plasma treated and 25-hydroxyvitamin $D_3$ loaded PCL fibers for 3 days, however, the cells expressed significantly higher level of hCAP 18 and LL-37 after incubation with plasma treated and 25-hydroxyvitamin $D_3$ loaded PCL fibers for 5 days. Additionally, it was revealed that $5.0 \times 10^{-6}$M 25-hydroxyvitamin $D_3$ caused cytotoxicity to U937 after culture for 3 and 5 days as part of monocytes could be killed or the proliferation could be inhibited under such a condition. Cytotoxicity is a concern in this cell line with $5.0 \times 10^{-6}$ M 25-hydroxyvitamin $D_3$ altering proliferation within 3 days. In a recent study, $5.0 \times 10^{-6}$ M or higher concentration of 25-hydroxyvitamin $D_3$ was demonstrated to be toxic to OKF6-TERT2 and little cytotoxicity was observed when the concentration was lower than $5.0 \times 10^{-7}$ M, which agrees with the foregoing results in U937 cells. So this concentration of 25-hydroxyvitamin $D_3$ was chosen as a control to test cytotoxicity and should be considered in applications to address surgical site infections. In comparison, the treatment of $5.0 \times 10^{-7}$ M free drug to HaCat and U937 cells failed to induce production of significant amount of hCAP 18 and LL-37. Plasma treated and 25-hydroxyvitamin $D_3$ loaded PCL fibers containing the same amount of 25-hydroxyvitamin $D_3$ can sustainably induce the production of hCAP 18 and LL-37 in both HaCat and U937 cells, emphasizing the importance of sustained release fiber formulations as a novel approach to optimize the biological environment. The results of antibacterial activity indicated that LL-37 in the lysis solutions of U937 cells treated with both $5.0 \times 10^{-6}$ M 25-hydroxyvitamin $D_3$ and plasma treated and 25-hydroxyvitamin $D_3$ loaded PCL fibers for 5 days could kill more bacteria than other treatment groups. EC50 of LL-37 against *Pseudomonas aeruginosa* is around 1.3 to 3.6 μg/ml, and this value against *Staphylococcus aureus* is 1.27 μg/ml. In the above-described study, there was no infection involved for cultured cells. Therefore, the production level of antimicrobial peptide in this study was relatively low. Even so, the studies demonstrated the antimicrobial activity of the present system in vitro. The results also indicated that the administration of plasma treated and 25-hydroxyvitamin $D_3$ loaded PCL fibers had no negative effects on the proliferation and simultaneously induced a high-level expression of hCAP 18 and LL-37 in human keratinocytes and monocytes, and LL-37 could kill bacteria to prevent infection, demonstrating a great usefulness in clinical applications. There is great need for a new approach to develop a post-surgical dressing that reduces the risk of surgical site infections. Current meta-analysis provides no evidence that current products reduce the risk of surgical site infections.

In summary, 25-hydroxyvitamin $D_3$ loaded PCL and PLA fibers were successfully prepared via electrospinning. Plasma treatment improved fiber hydrophilicity and promoted the release rate of 25-hydroxyvitamin $D_3$ from fibers. The 25-hydroxyvitamin $D_3$ release from PCL and PLA fibers can endure more than 28 days. The released 25-hydroxy vitamin $D_3$ from electrospun fibers can induce the production of a significantly higher level of hCAP 18/LL-37 than free drugs and LL-37 produced by monocytes could kill bacteria to prevent the occurrence of infection. Plasma treated and 25-hydroxyvitamin $D_3$ loaded PCL fibers were not exhibiting negative effects on the cell proliferation on human keratinocytes and monocytes. Therefore, the electrospun fibers developed in this study were thought to be useful as novel dressings for minimizing surgical site infections. These fibers can also be used as coating materials to the implants, devices or catheters for prevention of infections.

Throughout this document, various references are mentioned. All such references are incorporated herein by reference in their entirety, including the references set forth in the following list:

REFERENCES

1. Humes D J, Lobo D N. Antisepsis, asepsis and skin preparation. SurgOxf. 2009; 27(10): 441-5.
2. Reichman D E, Greenberg J A. Reducing Surgical Site Infections: A Review. Rev Obstet Gynecol. 2009; 2(4): 212-21.
3. Evans R P, Clyburn T A, Moucha C S, Prokuski L. Surgical Site Infection Prevention and Control: An Emerging Paradigm. Instr Course Lect. 2011; 60: 539-43.
4. Kohanski M A, Dwyer D J, Collins J J. How antibiotics kill bacteria: from targets to networks. Nat Rev Microbiol. 2010; 8(6): 423-35.
5. Peleg A Y, Seifert H, Paterson D L. *Acinetobacter baumannii*: Emergence of a Successful Pathogen. Clin Microbiol Rev. 2008; 21(3): 538-82.
6. Eliopoulos G M, Maragakis L L, Perl T M. *Acinetobacter baumannii*: Epidemiology, Antimicrobial Resistance, and Treatment Options. Clin Infect Dis. 2008; 46(8): 1254-63.
7. Esterly J, Richardson C L, Eltoukhy N S, Qi C, Scheetz M H. Genetic Mechanisms of Antimicrobial Resistance of *Acinetobacter baumannii* (Feb). Ann Pharmacother. 2011; DOI: 10.1345/aph.1P084.
8. Begum S, Hasan F, Hussain S, Ali Shah A. Prevalence of multi drug resistant *Acinetobacterbaumannii* in the clinical samples from Tertiary Care Hospital in Islamabad, Pakistan. Pak J Med Sci. 2013; 29(5): 1253-8.
9. Neville F, Cahuzac M, Konovalov O, Ishitsuka Y, Lee K Y C, Kuzmenko I, et al. Lipid Headgroup Discrimination by Antimicrobial Peptide LL-37: Insight into Mechanism of Action. Biophys J. 2006; 90(4): 1275-87.
10. Kemmis C M, Salvador S M, Smith K M, Welsh J. Human mammary epithelial cells express CYP27B1 and are growth inhibited by 25-hydroxyvitamin D-3, the major circulating form of vitamin D-3. J Nutr. 2006; 136(4): 887-92.
11. Seifert M, Tilgen W, Reichrath J. Expression of 25-hydroxyvitamin D-1alpha-hydroxylase (1alphaOHase, CYP27B1) splice variants in HaCaT keratinocytes and other skin cells: modulation by culture conditions and UV-B treatment in vitro. Anticancer Res. 2009; 29(9): 3659-67.
12. Viaene L, Evenepoel P, Meijers B, Vanderschueren D, Overbergh L, Mathieu C. Uremia suppresses immune signal-induced CYP27B1 expression in human monocytes. Am J Nephrol. 2012; 36(6): 497-508.
13. Pinzone M R, Di Rosa M, Celesia B M, Condorelli F, Malaguarnera M, Madeddu G, et al. LPS and HIV gp120 modulate monocyte/macrophage CYP27B1 and CYP24A1 expression leading to vitamin D consumption and hypovitaminosis D in HIV-infected individuals. Eur Rev Med Pharmacol Sci. 2013; 17(14): 1938-50.
14. Suzuki K, Murakami T, Kuwahara-Arai K, Tamura H, Hiramatsu K, Nagaoka I. Human anti-microbial cathelicidin peptide LL-37 suppresses the LPS-induced apoptosis of endothelial cells. Int Immunol. 2011; 23(3): 185-93.
15. Henzler Wildman K A, Lee D-K, Ramamoorthy A. Mechanism of Lipid Bilayer Disruption by the Human Antimicrobial Peptide, LL-37. Biochemistry. 2003; 42(21): 6545-58.
16. Zhang Z, Cherryholmes G, Shively J E. Neutrophil secondary necrosis is induced by LL-37 derived from cathelicidin. J Leukoc Biol. 2008; 84(3): 780-8.
17. Kahlenberg J M, Kaplan M J. Little Peptide, Big Effects: The Role of LL-37 in Inflammation and Autoimmune Disease. J Immunol. 2013; 191(10): 4895-901.
18. Steinstraesser L, Lam M C, Jacobsen F, Porporato P E, Chereddy K K, Becerikli M, et al. Skin Electroporation of a Plasmid Encoding hCAP-18/LL-37 Host Defense Peptide Promotes Wound Healing. Mol Ther. 2014; 22(4): 734-42.
19. Shringirishi M, Prajapati S K, Mahor A, Alok S, Yadav P, Verma A. Nanosponges: a potential nanocarrier for novel drug delivery-a review. Asian Pac. J. Trop. Dis. 2014; 4, Supplement 2: S519-26.
20. Xie J, Wang C-H. Electrospun micro- and nanofibers for sustained delivery of paclitaxel to treat C6 glioma in vitro. Pharm Res. 2006; 23(8): 1817-26.
21. Sill T J, von Recum H A. Electrospinning: Applications in drug delivery and tissue engineering. Biomaterials. 2008; 29(13): 1989-2006.
22. Choktaweesap N, Arayanarakul K, Aht-ongDuangdao, Meechaisue C, Supaphol P. Electrospun Gelatin Fibers: Effect of Solvent System on Morphology and Fiber Diameters. Polym J. 2007; 39(6): 622-31.
23. Hwang S H, Song J, Jung Y, Kweon O Y, Song H, Jang J. ElectrospunZnO/$TiO_2$ composite nanofibers as a bactericidal agent. Chem Commun. 2011; 47(32): 9164-6.
24. Maria Spasova D P. Electrospun chitosan-coated fibers of poly(L-lactide) and poly(L-lactide)/poly(ethylene glycol): preparation and characterization. Macromol Biosci. 2008; 8(2): 153-62.
25. Chen S, Wang G, Wu T, Zhao X, Liu S, Li G, et al. Silver nanoparticles/ibuprofen-loaded poly(L-lactide) fibrous membrane: anti-infection and anti-adhesion effects. Int J Mol Sci. 2014; 15(8): 14014-25.
26. Mohiti-Asli M, Pourdeyhimi B, Loboa E G. Novel, silver-ion-releasing nanofibrous scaffolds exhibit excellent antibacterial efficacy without the use of silver nanoparticles. Acta Biomater. 2014; 10(5): 2096-104.
27. Woodruff M A, Hutmacher D W. The return of a forgotten polymer—Polycaprolactone in the 21st century. Prog Polym Sci. 2010; 35(10): 1217-56.
28. Lin Xiao B W. Poly(Lactic Acid)-Based Biomaterials: Synthesis, Modification and Applications, Dhanjoo N G, editors. Biomedical science, engineering and technology. Rijeka: Intech. 2012. p. 247-279
29. Xie J, Willerth S M, Li X, Macewan M R, Rader A, Sakiyama-Elbert S E, et al. The differentiation of embryonic stem cells seeded on electrospun nanofibers into neural lineages. Biomaterials. 2009; 30(3): 354-62.
30. Xie J, Liu W, MacEwan M R, Bridgman P C, Xia Y. Neurite Outgrowth on Electrospun Nanofibers with Uniaxial Alignment: The Effects of Fiber Density, Surface Coating, and Supporting Substrate. ACS Nano. 2014; 8(2): 1878-85.
31. Jiang J, Xie J, Ma B, Bartlett D E, Xu A, Wang C-H. Mussel-inspired protein-mediated surface functionalization of electrospun nanofibers for pH-responsive drug delivery. Acta Biomater. 2014; 10(3): 1324-32.
32. Harbarth S, Samore M H, Lichtenberg D, Carmeli Y. Prolonged antibiotic prophylaxis after cardiovascular surgery and its effect on surgical site infections and antimicrobial resistance. Circulation. 2000; 101(25): 2916-21.
33. Liu P T, Stenger S, Li H, Wenzel L, Tan B H, Krutzik S R, et al. Toll-like receptor triggering of a vitamin D-mediated human antimicrobial response. Science. 2006; 311 (5768): 1770-3.
34. Selsted M E, Ouellette A J. Mammalian defensins in the antimicrobial immune response. Nat Immunol. 2005; 6(6): 551-7.
35. Yuk J-M, Shin D-M, Lee H-M, Yang C-S, Jin H S, Kim K-K, et al. Vitamin D3 Induces Autophagy in Human Monocytes/Macrophages via Cathelicidin. Cell Host Microbe. 2009; 6(3): 231-43.
36. Sorensen O E, Follin P, Johnsen A H, Calafat J, Tjabringa G S, Hiemstra P S, et al. Human cathelicidin, hCAP-18, is processed to the antimicrobial peptide LL-37 by extracellular cleavage with proteinase 3. Blood. 2001; 97(12): 3951-9.
37. Strempel N, Neidig A, Nusser M, Geffers R, Vieillard J, Lesouhaitier O, et al. Human Host Defense Peptide LL-37 Stimulates Virulence Factor Production and Adaptive Resistance in *Pseudomonas aeruginosa*. PLoS One. 2013; 8(12): e82240.
38. Love J F, Tran-Winkler H J, Wessels M R. Vitamin D and the Human Antimicrobial Peptide LL-37 Enhance Group A *Streptococcus* Resistance to Killing by Human Cells. Mbio. 2012; 3(5): e00394-12.
39. Gombart A F, Borregaard N, Koeffler H P. Human cathelicidin antimicrobial peptide (CAMP) gene is a direct target of the vitamin D receptor and is strongly up-regulated in myeloid cells by 1,25-dihydroxyvitamin D3. FASEB J. 2005; 19(9): 1067-77.
40. Dixon B M, Barker T, McKinnon T, Cuomo J, Frei B, Borregaard N, et al. Positive correlation between circulating cathelicidin antimicrobial peptide (hCAP18/LL-37) and 25-hydroxyvitamin D levels in healthy adults. BMC Res Notes. 2012; 5(1): 575.
41. Persons K S, Eddy V J, Chadid S, Deoliveira R, Saha A K, Ray R. Anti-growth effect of 1,25-dihydroxyvitamin D3-3-bromoacetate alone or in combination with 5-amino-imidazole-4-carboxamide-1-beta-4-ribofuranoside in pancreatic cancer cells. Anticancer Res. 2010; 30(6): 1875-80.
42. Schauber J, Dorschner R A, Coda A B, Buchau A S, Liu P T, Kiken D, et al. Injury enhances TLR2 function and antimicrobial peptide expression through a vitamin D-dependent mechanism. J Clin Invest. 2007; 117(3): 803-11.
43. Ishii D, Ying T H, Mahara A, Murakami S, Yamaoka T, Lee W, et al. In Vivo Tissue Response and Degradation Behavior of PLLA and Stereocomplexed PLA Nanofibers. Biomacromolecules. 2009; 10(2): 237-42.
44. Rosa D S, Lopes D R, Calil M R. Thermal properties and enzymatic degradation of blends of poly(ε-caprolactone) with starches. Polym Test. 2005; 24(6): 756-61.
45. Masaki K, Kamini N R, Ikeda H, Iefuji H. Cutinase-Like Enzyme from the Yeast *Cryptococcus* sp. Strain S-2 Hydrolyzes Polylactic Acid and Other Biodegradable Plastics. Appl Environ Microbiol. 2005; 71(11): 7548-50.
46. Wang Q, Zhang W, Li H, Aprecio R, Wu W, Lin Y, et al. Effects of 25-hydroxyvitamin $D_3$ on cathelicidin production and antibacterial function of human oral keratinocytes. Cell Immunol. 2013; 283(1-2): 45-50.

47. Dumville J C, Gray T A, Walter C J, Sharp C A, Page T. Dressings for the prevention of surgical site infection. *The Cochrane database of systematic reviews.* 2014; 9:CD003091.

48. Shroff R, Knott C, Rees L. The virtues of vitamin D—but how much is too much? *Pediatr Nephrol* 2010; 25:1607-1620.

49. Norman A. Sunlight, season, skin pigmentation, vitamin D, and 25-hydroxyvitamin D: integral components of the vitamin D endocrine system. *Am J Clin Nutr* 1998; 67:1108-1110.

50. Gombart A. The vitamin D-antimicrobial peptide pathway and its role in protection against infection. *Fut Microbiol* 2009; 4:1151.

51. Webb A R, Kift R, Durkin M T, et al. The role of sunlight exposure in determining the vitamin D status of the U.K. white adult population. *Brit J Dermatol* 2010; 163:1050-1055.

52. Calvo M, Whiting S, Barton C Vitamin D intake: a global perspective of current status. *J Nutrl* 2005; 135: 310-316.

53. Spector, S. Vitamin D and HIV: letting the sun shine in. *Top Antivir Med* 2011; 19(1):6-10.

54. Schwalfenberg, G. K. A review of the critical role of vitamin D in the functioning of the immune system and the clinical implications of vitamin D deficiency. *Mol Nutr and Food Res* 2010; 55:96-98.

55. Braff M H, Gallo R L Antimicrobial peptides: an essential component of the skin defensive barrier. *Curr Top Microbiol Immunol* 2006; 306:91-110.

56. White, J. H. Vitamin D as an inducer of cathelicidin antimicrobial peptide expression: Past, present and future. *J Steroid Biochem Mol Biol* 2010; 121:234-238.

57. Hewison, M. Antibacterial effects of vitamin D. *Nat Rev Endocrinol* 2011; 7:337-345.

58. Hewison, M. Vitamin D and the immune system: new perspectives on an old theme. *Endocrin Metab Clin* 2010; 39(2):265-379.

59. Andrewes C. *The Common Cold.* New York: Norton, 1965.

60. Shadrin A S, Marinich I G, Taros L Y. Experimental and epidemiological estimation of seasonal and climatogeographical features of non-specific resistance of the organism to influenza. *J Hyg Epid Microb Im* 1977; 21:155-161.

61. Hope-Simpson R. The role of season in the epidemiology of influenza. *J Hyg* 1981; 86(1): 35-47.

62. Cannell J, Vieth R, Umhau C, et al. Epidemic influenza and vitamin D. *Epidemiol Infect* 2006; 134(6): 1129-1140.

63. Grant, W. B. Solar ultraviolet-B irradiance and vitamin D may reduce the risk of septicemia. *Dermatoendocrinol* 2008; 1(1):37-42.

64. Watkins R R, Yamshchikov A V, Lemonvich T L, Salata R A. The role of vitamin D deficiency in sepsis and potential therapeutic implications. *J Infect* 2011; 63:321-326.

65. Aloia J, Li-ng M. Correspondence. *Epidemiol Infect* 2007; 135(7): 1095-1098.

66. Barclay L, Lie D, Martin B Vitamin D levels may be inversely linked with recent upper respiratory tract infection. *Arch Intern Med* 2009; 169:384-390.

67. National Academy of Science. Dietary Reference Intakes for Calcium, Magnesium, Phosphorus, Vitamin D, and Fluoride. Washington, D.C.: National Academies Press; 1999.

68. Lappe J M, Travers-Gustafson D, Davies K M, et al. Vitamin D and calcium supplementation reduces cancer risk: results of a randomized trial. *Am J Clin Nutr* 2007; 85:1586-1591.

69. Holick M F. Vitamin D deficiency. *N Engl J Med* 2007 357:266-281.

70. Zehnder D, Bland R, Williams M C, et al. Extrarenal expression of 25-hydroxyvitamin d(3)-1 alpha-hydroxylase. *J Clin Endocrinol Metab.* 2001; 86(2):888-94.

71. Jiang J, Chen G, Shuler F D, Wang C-H and Xie J. 2015. Local sustained delivery of 25-hydroxyvitamin D3 for prevention of surgical site infections. Pharm Res. 2015 Mar. 14. PMID: 25773720.

It will be understood that various details of the presently-disclosed subject matter can be changed without departing from the scope of the subject matter disclosed herein. Furthermore, the foregoing description is for the purpose of illustration only, and not for the purpose of limitation.

What is claimed is:

1. A wound covering, comprising:
   a substrate including one or more fibers comprised of a polymer; and
   vitamin D, or analogues or metabolites thereof, embedded in the one or more fibers such that the vitamin D, or analogues or metabolites thereof, is present within the one or more fibers, and
   wherein the one or more fibers including the vitamin D, or analogues or metabolites thereof, embedded therein are electrospun fibers produced by an electrospinning process.

2. The wound covering of claim 1, wherein the polymer includes poly($\epsilon$-caprolactone) (PCL), poly($_L$-lactide) (PLA), cellulose, or combinations thereof.

3. The wound covering of claim 1, wherein the electrospun fiber is plasma-treated.

4. The wound covering of claim 1, wherein the one or more fibers form a mesh.

5. The wound covering of claim 1, wherein the one or more fibers form a wound dressing.

6. The wound covering of claim 1, wherein the wound covering is biodegradable.

7. The wound covering of claim 1, wherein the wound covering is biocompatible.

8. The wound covering of claim 1, wherein the wound covering is configured to release the vitamin D, or analogues or metabolites thereof, under physiological conditions for at least about 1 day to about 50 days.

9. The wound covering of claim 1, further comprising a bioactive agent.

10. The wound covering of claim 9, wherein the bioactive agent is selected from antibiotics, anti-inflammatories, and combinations thereof.

11. A method for making a wound covering, comprising:
    providing a solution that includes a polymer;
    adding vitamin D, or analogues or metabolites thereof, to the solution to form a mixture; and
    forming one or more fibers from the mixture that are embedded with the vitamin D, or analogues or metabolites thereof, such that the vitamin D, or analogues or metabolites thereof, is embedded within the one or more fibers, and
    wherein forming the one or more fibers including the vitamin D, or analogues or metabolites thereof, embedded therein comprises forming the one or more fibers by an electrospinning process such that the formed fibers are electrospun fibers.

12. The method of claim 11, further comprising a step of exposing the one or more fibers to a plasma treatment.

13. A method of treating a subject, comprising applying a wound covering to a site on a subject, the wound covering including one or more fibers that are embedded with vitamin D, or analogues or metabolites thereof, such that the vitamin D, or analogues or metabolites thereof, is present within the one or more fibers,
   wherein the one or more fibers including the vitamin D, or analogues or metabolites thereof, embedded therein are electrospun fibers produced by an electrospinning process.

14. The method of claim 13, wherein the site on the subject is a surgical site.

15. The method of claim 13, wherein the site on the subject is a site of a tissue injury or wound.

16. The method of claim 13, wherein applying the wound covering increases an amount of an antimicrobial peptide in the subject.

17. The method of claim 16, wherein the antimicrobial peptide is selected from hCAP18 and LL-37.

18. The wound covering of claim 1, wherein the vitamin D comprises 25-hydroxyvitamin D (25(OH)D).

\* \* \* \* \*